(12) United States Patent
Hanein et al.

(10) Patent No.: US 12,070,597 B2
(45) Date of Patent: Aug. 27, 2024

(54) DEVICE AND METHOD FOR NEUROSTIMULATION

(71) Applicants: RAMOT AT TEL-AVIV UNIVERSITY LTD., Tel Aviv (IL); UNIVERSITAET LINZ, Linz (AT)

(72) Inventors: Yael Hanein, Cesarea (IL); Niyazi Serdar Sariciftci, Linz (AT); Eric Daniel Glowacki, Warsaw (PL); David Rand, Nes-Ziona (IL); Gur Lubin, Tel Aviv-Jaffa (IL); Marie Jakesova, Brno-Ivanovice (CZ)

(73) Assignees: RAMOT AT TEL-AVIV UNIVERSITY LTD., Tel Aviv (IL); UNIVERSITAET LINZ, Linz (AT)

(*) Notice: Subject to any disclaimer, the term of this patent is extended or adjusted under 35 U.S.C. 154(b) by 1101 days.

(21) Appl. No.: 16/766,978

(22) PCT Filed: Nov. 26, 2018

(86) PCT No.: PCT/IL2018/051283
§ 371 (c)(1),
(2) Date: May 26, 2020

(87) PCT Pub. No.: WO2019/102478
PCT Pub. Date: May 31, 2019

(65) Prior Publication Data
US 2020/0316370 A1 Oct. 8, 2020

Related U.S. Application Data

(60) Provisional application No. 62/590,590, filed on Nov. 26, 2017.

(51) Int. Cl.
*A61N 1/05* (2006.01)
*A61N 1/36* (2006.01)
(Continued)

(52) U.S. Cl.
CPC ....... *A61N 1/0543* (2013.01); *A61N 1/36046* (2013.01); *H10K 30/20* (2023.02);
(Continued)

(58) Field of Classification Search
None
See application file for complete search history.

(56) References Cited

U.S. PATENT DOCUMENTS 6,230,057 B1 * 5/2001 Chow .................. A61N 1/05
607/148
6,298,270 B1 * 10/2001 Nisch .................. A61N 1/0543
607/54

(Continued)

OTHER PUBLICATIONS

Agbolaghi et al., A comprehensive review on poly(3-alkylthiophene)-based crystalline structures, protocols and electronic applications, Organic Electronics, 51 (2017) 362-403 (Year: 2017).*

(Continued)

*Primary Examiner* — Carl H Layno
*Assistant Examiner* — Manolis Pahakis
(74) *Attorney, Agent, or Firm* — Vorys, Sater, Seymour and Pease LLP; Anthony P. Venturino; Maryellen Feehery Hank

(57) ABSTRACT

An efficient nanoscale semiconducting optoelectronic system, containing a P/N acceptor donor organic hetrojunction which is optimized for neuronal stimulation—an organic electrolytic photocapacitor. The devices comprise a thin (80 nm) trilayer of metal and p-n semiconducting organic nanocrystals. When illuminated in physiological solution, these metal-semiconductor devices charge up, transducing light pulses into localized displacement currents that are strong enough to electrically stimulate neurons with safe light intensities.

18 Claims, 15 Drawing Sheets

(51) Int. Cl.
*H10K 30/20* (2023.01)
*H10K 85/30* (2023.01)
*H10K 85/60* (2023.01)

(52) U.S. Cl.
CPC ........ *A61N 1/0551* (2013.01); *A61N 1/36062* (2017.08); *H10K 85/311* (2023.02); *H10K 85/621* (2023.02)

(56) References Cited

U.S. PATENT DOCUMENTS

| | | | |
|---|---|---|---|
| 8,725,266 B2* | 5/2014 | Olson | A61K 41/00 607/54 |
| 9,037,251 B2* | 5/2015 | Narayan | B82Y 10/00 607/116 |
| 9,114,004 B2* | 8/2015 | Fan | A61N 1/0543 |
| 9,198,753 B2* | 12/2015 | Gefen | A61F 9/00 |
| 9,322,713 B2* | 4/2016 | Narayan | H10K 30/30 |
| 9,345,568 B2* | 5/2016 | Cho | A61N 1/0543 |
| 9,425,254 B1* | 8/2016 | Gross | B82Y 20/00 |
| 9,610,456 B2* | 4/2017 | Linke | A61N 1/0543 |
| 9,925,368 B2* | 3/2018 | Ryu | A61N 1/0534 |
| 10,121,533 B2* | 11/2018 | Liran | G11C 5/143 |
| 10,603,493 B2* | 3/2020 | Silva | G01N 21/6456 |
| 2006/0180199 A1 | 8/2006 | Lenhard et al. | |
| 2008/0288067 A1* | 11/2008 | Flood | H10K 85/225 623/6.63 |
| 2009/0004471 A1* | 1/2009 | Amthor | A61B 5/388 428/375 |
| 2009/0292325 A1* | 11/2009 | Cederna | A61L 27/34 607/2 |
| 2010/0065829 A1* | 3/2010 | Forrest | H10K 30/30 257/40 |
| 2010/0185260 A1* | 7/2010 | Olson | A61K 9/0051 607/54 |
| 2010/0249877 A1* | 9/2010 | Naughton | B82Y 15/00 607/54 |
| 2010/0282309 A1* | 11/2010 | Pschirer | B82Y 10/00 136/262 |
| 2011/0201994 A1* | 8/2011 | Peyman | A61K 31/337 604/20 |
| 2011/0270153 A1* | 11/2011 | Olson | A61N 1/36046 604/20 |
| 2012/0136296 A1* | 5/2012 | Peyman | A61K 41/00 604/20 |
| 2012/0197364 A1* | 8/2012 | Banin | A61N 1/0543 977/925 |
| 2012/0313080 A1 | 12/2012 | Boulais et al. | |
| 2013/0023986 A1* | 1/2013 | Keller | A61N 1/0543 438/85 |
| 2013/0184783 A1 | 7/2013 | Antognazza et al. | |
| 2013/0226268 A1* | 8/2013 | Pan | A23L 3/26 422/291 |
| 2013/0309278 A1* | 11/2013 | Peyman | A61F 9/0079 435/375 |
| 2013/0324909 A1* | 12/2013 | Aydt | A61P 17/02 604/20 |
| 2014/0056815 A1* | 2/2014 | Peyman | A61K 49/085 424/9.4 |
| 2014/0128972 A1* | 5/2014 | Khraiche | A61N 1/0543 438/73 |
| 2014/0330337 A1* | 11/2014 | Linke | H01L 31/042 607/45 |
| 2015/0037203 A1* | 2/2015 | Pan | A61N 5/0616 257/40 |
| 2015/0119794 A1* | 4/2015 | Peyman | A61N 5/0622 604/20 |
| 2015/0283265 A1 | 10/2015 | Peyman | |
| 2015/0295195 A1* | 10/2015 | Pfeiffer | H10K 30/82 136/255 |
| 2016/0082272 A1* | 3/2016 | Karst | H01L 31/0322 320/101 |
| 2016/0213926 A1* | 7/2016 | Fukuma | A61N 1/0543 |
| 2017/0005283 A1* | 1/2017 | Al-Ghamdi | H10K 71/12 |
| 2020/0038680 A1* | 2/2020 | Degenaar | A61N 5/0601 |
| 2020/0316370 A1* | 10/2020 | Hanein | H10K 30/20 |

OTHER PUBLICATIONS

Triyana et al., "Tandem-type organic solar cells by stacking different heterojunction materials", Thin Solid Films, Elsevier, Amsterdam, NL, vol. 477, No. 1-2, 2005, pp. 198-202.

Abdullaeva et al., "Photoelectrical Stimulation of Neuronal Cells by an Organic Semiconductor-Electrolyte Interface", Langmuir, 2016, vol. 32, pp. 8533-8542.

Bareket et al., "Semiconductor Nanorod-Carbon Nanotube Biomimetic Films for Wire-Free Photostimulation of Blind Retinas", Nano Lett., 2014, vol. 14, No. 11, pp. 6685-6692.

Gautam et al., "A Polymer Optoelectronic Interface Provides Visual Cues to a Blind Retina", Adv. Mater., 2014, vol. 26, No. 11, pp. 1751-1756.

Ghezzi et al., "A hybrid bioorganic interface for neuronal photoactivation", Nature Communications, 2011, vol. 2, No. 1, p. 166, 7 pages total.

Ghezzi et al., "A polymer optoelectronic interface restores light sensitivity in blind rat retinas", Nature Photonics, 2013. vol. 7, pp. 400-406.

Martino et al., "Photothermal cellular stimulation in functional bio-polymer interfaces", Scientific Reports, 2015, vol. 5, p. 8911, eight pages total.

Maya-Vetencourt et al., "A fully organic retinal prothesis restores vision in a rat model of degenerative blindness", Nature Materials, 2017, vol. 16, No. 6, pp. 681-689.

Peumans et al., "Small molecular weight organic thin-film photodetectors and solar cells", J. Appl. Phys., 2003, vol. 93, No. 7, pp. 3693-3723. (Reference Split Into 2 Segments).

Sytnyk et al., "Hydrogen-Bonded Organic Semiconductor Micro- and Nanocrystals: From Colloidal Syntheses to (Opto-)Electronic Devices", Journal of the American Cancer Society, 2014, vol. 136, No. 47, pp. 16522-16532.

Sytnyk et al., "Cellular interfaces with hydrogen-bonded organic semiconductor hierarchical nanocrystals", Nature Communications, 2017, vol. 8, No. 1, p. 91, 11 pages total.

\* cited by examiner

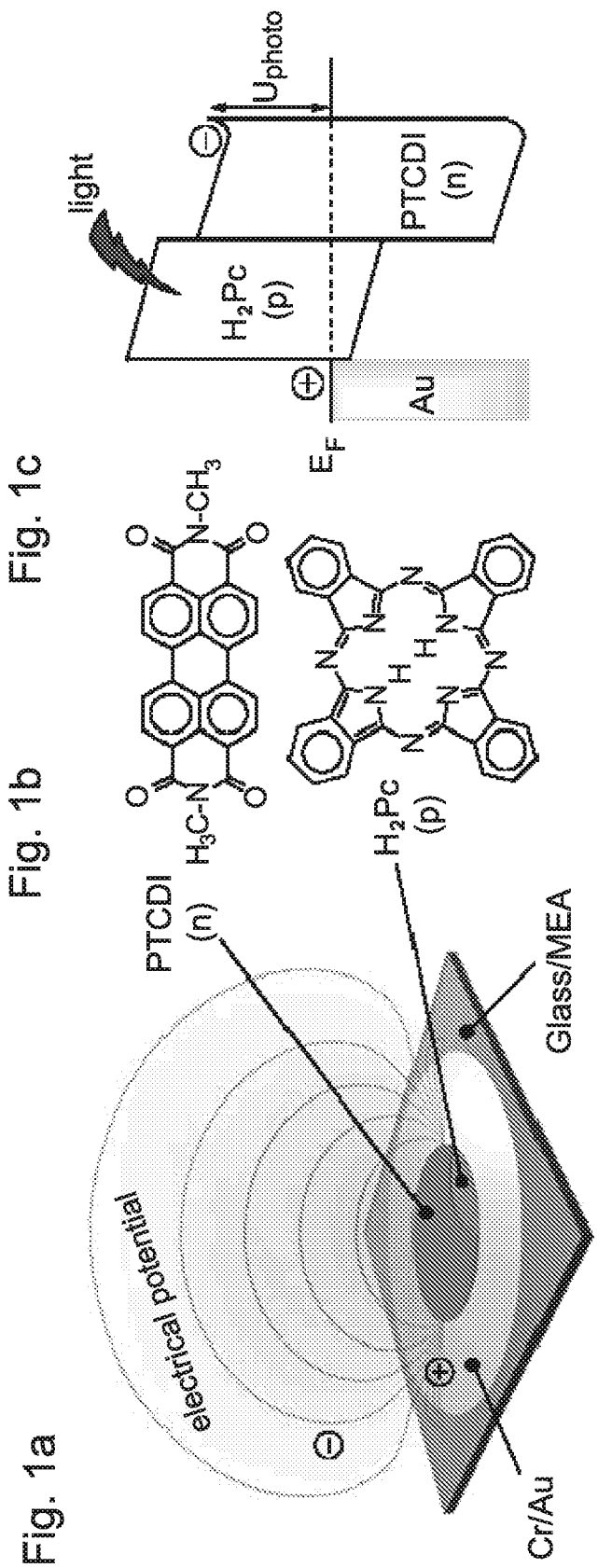

Type I

Fig. 3a Control
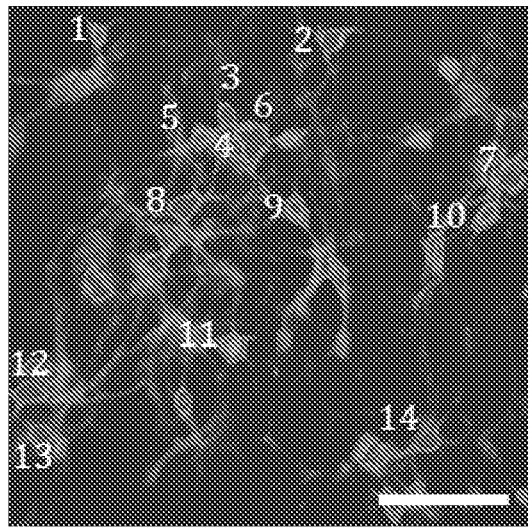
Fig. 3b Cr/Au/H$_2$Pc/PTCDI
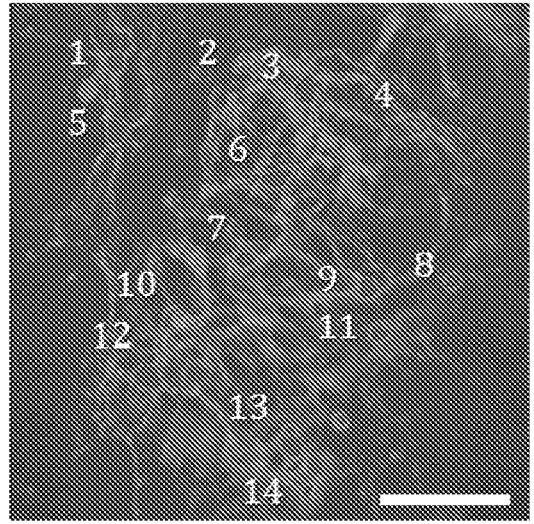
Fig. 3c
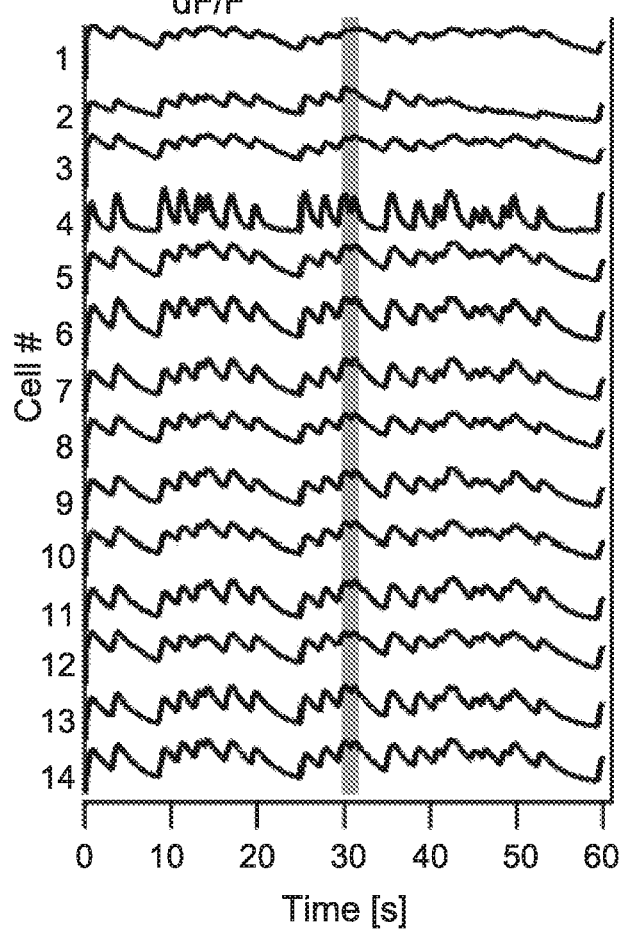
Fig. 3d
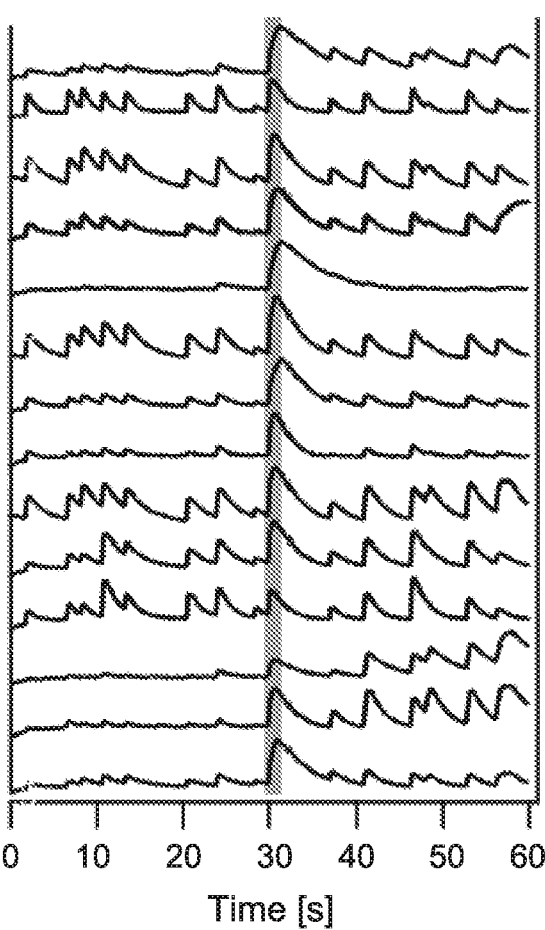

y=-0.798x(α= -38.6°)
y=-0.781x(α= -37.9°)   500 μm

50 μm

50 μm

-76°   -38°   0°   38°   76°

Fibers directionality ms

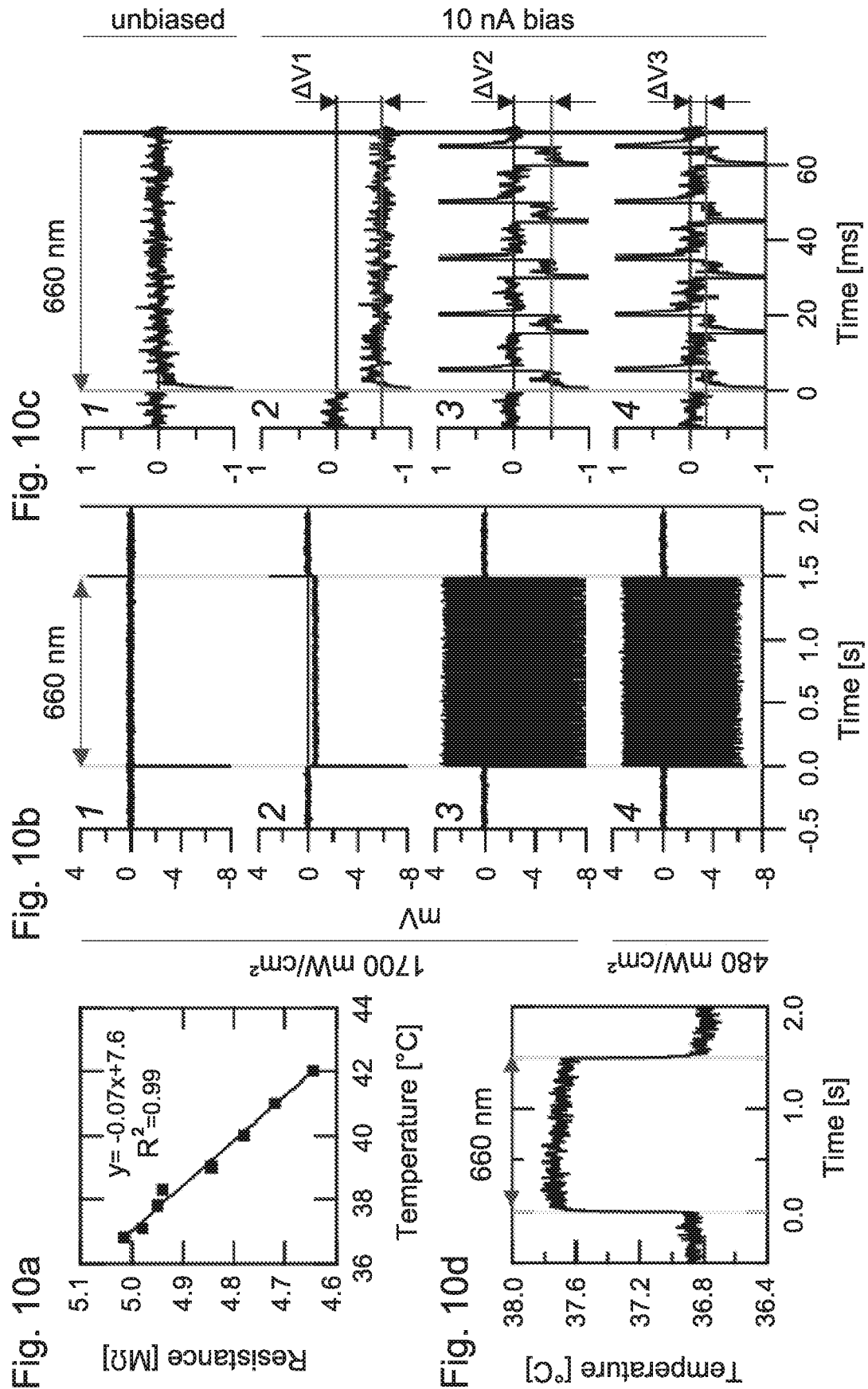

DEVICE AND METHOD FOR NEUROSTIMULATION

CROSS-REFERENCE TO RELATED APPLICATIONS

This application is a national stage of PCT/IL2018/051283 filed on Nov. 26, 2018, which claims the benefit of priority from U.S. Provisional Application No. 62/590,590 filed on Nov. 26, 2017, herein incorporated by reference.

TECHNOLOGICAL FIELD

The invention generally concerns devices and methods for neurostimulation of tissues in a living animal body.

BACKGROUND

Stimulation of neurons in a localized and safe manner is important both as an investigative tool as well as a therapeutic means. A wide range of biomedical engineering technologies have been developed to electrically communicate with neurons, including direct electrical stimulation with conducting electrodes and ion delivery devices, radiation with infrared light and genetic manipulation of cells. Eliminating the need for wiring, optical stimulation is an elegant solution, which is inherently less invasive. In particular, non-genetic approaches to impart long-term selective photosensitivity to electrophysiological processes are highly desired for in vivo applications in humans.

Optoelectronic diodes, which interconvert optical and electrical pulses, are a mature technology at the crux of modern civilization. Deploying such devices in the biological context, however, is not at all straightforward. Optoelectronics are optimized to work in dry conditions, and electrical interconnects as well as many semiconductor materials corrode in a physiological setting. Moreover, these devices are hard and rigid, and create difficulties from poor biocompatibility, such as scar tissue formation. Despite the clear need for non-genetic means to optically stimulate neurons, the range of available devices suitable to facilitate neuronal response under illumination is limited and silicon optoelectronics have been the primary platform in emerging applications, among them neuronal stimulation applications and in particular artificial retinal devices, some of which are in clinical trials or already on the market.

Despite the clear advantages associated with the use of silicon-based devices, they are rigid and poorly suited to interface with soft and often sensitive biological tissues. Silicon, as an indirect band gap semiconductor, has a low absorbance coefficient, and therefore thickness of tens to hundreds of µm of silicon is necessary to absorb light efficiently, which sets a high lower-limit for overall device thickness. Moreover, silicon-based devices suffer from stability and passivation problems in physiological conditions.

Organic semiconducting polymers have shown the ability to photostimulate neurons, and explanted retinas and there is evidence that implanted films can restore light sensitivity to blind retinas in vivo. Semiconducting nanocrystals have also been successfully deployed for retinal stimulation. These suggested systems boast ease of fabrication as well as flexibility, the ability to operate in a wet environment without extensive passivation/encapsulation, and biocompatibility. However, the stimulating mechanism underlying the observations of these new systems was often stated not to be fully elucidated, or the effects are primarily photothermal in nature. For example, photogenerated charge density values are often too low (<1 µC/cm$^2$) to substantiate electrical stimulation. Semiconducting polymer and inorganic nanocrystal systems can stimulate explanted retinas, however only delayed or latent responses are recorded.

BACKGROUND ART

[1] Bareket, L., Waiskopf, N., Rand, D., Lubin, G., David-Pur, M., Ben-Dov, J., Hanein, Y. (2014). Semiconductor Nanorod-Carbon Nanotube Biomimetic Films for Wire-Free Photostimulation of Blind Retinas. Nano Letters, 14(11), 6685-6692.

[2] Gautam, V., Rand, D., Hanein, Y., & Narayan, K. S. (2014). A Polymer Optoelectronic Interface Provides Visual Cues to a Blind Retina. Advanced Materials, 26(11), 1751-1756.

[3] Ghezzi, D., Antognazza, M. R., Dal Maschio, M., Lanzarini, E., Benfenati, F., & Lanzani, G. (2011). A hybrid bioorganic interface for neuronal photoactivation. Nature Communications, 2(1), 166.

[4] Ghezzi, D., Antognazza, M. R., Maccarone, R., Bellani, S., Lanzarini, E., Martino, N., Benfenati, F. (2013). A polymer optoelectronic interface restores light sensitivity in blind rat retinas. Nature Photonics, (March), 1-7.

[5] Martino, N., Feyen, P., Porro, M., Bossio, C., Zucchetti, E., Ghezzi, D., Antognazza, M. R. (2015). Photothermal cellular stimulation in functional bio-polymer interfaces. Scientific Reports, 5, 8911.

[6] Maya-Vetencourt, J. F., Ghezzi, D., Antognazza, M. R., Colombo, E., Mete, M., Feyen, P., Benfenati, F. (2017). A fully organic retinal prosthesis restores vision in a rat model of degenerative blindness. Nature Materials, 16(6), 681-689.

[7] Abdullaeva, O. S. et al. Photoelectrical Stimulation of Neuronal Cells by an Organic Semiconductor-Electrolyte Interface. Langmuir 32, 8533-8542 (2016).

[8] Sytnyk, M., Glowacki, E. D., Yakunin, S., Voss, G., Schdfberger, W., Kriegner, D., Heiss, W. (2014). Hydrogen-Bonded Organic Semiconductor Micro- And Nanocrystals: From Colloidal Syntheses to (Opto-)Electronic Devices. Journal of the American Chemical Society, 136 (47), 16522-16532.

[9] Sytnyk, M., Jakesovi, M., Litviiiukovi, M., Mashkov, O., Kriegner, D., Stangl, J., Glowacki, E. D. (2017). Cellular interfaces with hydrogen-bonded organic semiconductor hierarchical nanocrystals. Nature Communications, 8(1), 91.

[10] Peumans, P., Yakimov, A. & Forrest, S. R. Small molecular weight organic thin-film photodetectors and solar cells. J. Appl. Phys. 93, 3693 (2003).

GENERAL DESCRIPTION

A fundamental requirement in designing photosensitive devices for neuronal stimulation is a high conversion efficiency of light into a capacitive displacement current sufficient for cell depolarization. A photosensitive device should also be biocompatible and ideally simple to fabricate in a scalable way with as small as possible dimensions and weight.

To engineer a device that meets the aforementioned prerequisites, the inventors of the technology disclosed herein have developed pigment-based devices that comprise organic crystalline semiconductor p-n/n-p heterojunctions that operate as photocapacitors. The devices of the invention are not only stable, but also meet the properties necessary for cellular stimulation, for example efficient charge photogeneration, minimal footprint, and lack of Faradaic processes. The generation of sufficiently large photovoltages and displacement currents enables capacitive stimulation of excitable cells.

The efficacy of the organic photocapacitor technology of the invention has been demonstrated by stimulating primary neurons with short light impulses. These studies establish the stability of the organic devices and their lack of detrimental effects on cell viability. Further, thermal effects have been excluded.

While devices of the invention may be used to neurostimulate a variety of living animal tissues, the effectivity and usability of the devices is demonstrated herein on explanted light-insensitive retinas, unambiguously proving direct photoelectrical stimulation using short light-pulses (1-5 ms). Devices according to the invention afford retinal stimulation with parameters on-par with mature silicon-based technologies; yet, in contrast to silicon-based devices, the devices of the invention are three-orders of magnitude thinner, and further are implemented with a semiconductor layer that comes in direct contact with cells, without any passivation.

Thus, in a general aspect of the invention, there is provided a device for neurostimulating a tissue, the device being an efficient nanoscale semiconducting optoelectronic system optimized for neuronal stimulation. Devices of the invention comprise a multilayer (or are constructed in a multi-layered form/structure), typically a tri-layer (typically thin, about 80 nm in thickness) of at least one metal or conductive material and p-n/n-p structure layered thereon. The p-n/n-p structure comprises semiconducting organic nanocrystals. When illuminated, e.g., in a physiological solution, the metal-semiconductor devices operate as photocapacitors, transducing light pulses into localized displacement currents that are strong enough to electrically stimulate neurons in a tissue placed at the vicinity of the device (in contact therewith). The electrical stimulation is accomplished with safe light intensities that are one hundred times below the safe ocular limit at 660 nm. The devices are freestanding, requiring no wiring or external bias, and are biocompatible and stable in physiological conditions.

In some embodiments, the multi-layered structure comprises two layers (a bilayer), three layers (a tri-layer) or four or more layers.

The semiconductor layers of the p-n/n-p structure are made of or composed of ubiquitous and nontoxic pigments, fabricated via simple and scalable deposition techniques.

Thus, in a first aspect there is provided a photoresponse device comprising a metal or a conductive material layer and a p-n/n-p structure being in continuous contact (direct contact) with the metal or conductive material layer. The p-n/n-p structure comprises a combination of two or more organic semiconductor pigments, at least one being selected amongst electron donor materials (a p-type material) and at least one other being selected amongst electron accepting materials (an n-type material).

In some embodiments, the photoresponse device is a multi-layered structure comprising a metal layer or a conductive material layer, a layer of at least one light-absorbing (electron donor) material that is in continues (direct) contact with the metal or conductive material layer and a layer of at least one electron acceptor material that is in continuous (direct) contact with the layer of the at least one light-absorbing material.

In other embodiments, the photoresponse device is a multi-layered structure comprising a metal layer or conductive material layer, a layer of at least one electron acceptor material that is in continues (direct) contact with the metal or conductive material layer and a layer of at least one light-absorbing (electron donor) material that is in continuous (direct) contact with the layer of the at least one electron acceptor material.

In some embodiments, the device comprises a substrate, at least one metal or conductive material layer formed onto one or more regions of the substrate, and a p-n/n-p structure, as defined herein, formed on at least one of the metal layer or metal regions.

In some embodiments, the device comprises a metal or a conductive material layer, a layer consisting of at least one p-type organic pigment material or a layer consisting of at least one n-type organic pigment material that is stacked onto at least a region of said metal layer.

In some embodiments, the photoresponse device is a photocapacitor.

The invention further provides a photoresponse device configured as an organic crystalline semiconductor p-n/n-p heterojunction that in physiological environment operates as a photocapacitor.

The invention also provides a photocapacitor device for responding to a light of a selected wavelength, said device comprising a first region comprising at least one metal or conductive material; and a second region composed of a p-n/n-p structure, as defined herein. In some embodiments, the first region is formed on a substrate in the form of a layer or a film onto which the second region, being in the form of a film structure or a multi-layered structure, is formed.

As used herein, a "p-n/n-p structure" is a layered stacked structure comprising a layer of one organic semiconductor pigment and another layer of a different organic semiconductor pigment. The structure may be of either p-n polarity, or n-p polarity.

In some embodiments, the structure is a p-n structure wherein the layer being in direct contact with the metal or the conductive material layer is a "p-type layer" consisting at least one material selected amongst electron donor materials, The layer being in direct contact with the p-type layer is an "n-type layer" consisting at least material selected amongst electron accepting materials. The n-type layer is a top-most layer that comes into contact with the tissue or cell to be stimulated or excited.

In some embodiments, the structure is a n-p structure wherein the above p-type layer/n-type layer structure is reversed. In other words, the layer being in direct contact with the metal or conductive material layer is an n-type layer and the layer being in direct contact with the n-type layer is a p-type layer. The p-type layer is a top-most layer that comes into contact with the tissue or cell to be stimulated or excited.

In some embodiments, the p-n/n-p structure substantially completely or fully covers the metal or conductive material layer, or is layered in spaced-apart regions on the metal or conductive material layer to form an array of p-n/n-p regions or p-n/n-p islands or p-n/n-p pixels on the metal layer or conductive material layer. While each p-n/n-p region, island or pixel may vary in size, shape and position on the metal or conductive material layer, the p-type layer is always in direct contact with the metal or conductive material. Where the metal or the conductive material layer is not continuously layered on the substrate, but is rather formed in spaced-apart regions thereon, each region may be covered with the p-n/n-p structure, completely or in the form of islands or pixels, as detailed herein. In some embodiments, the metal layer is randomly decorated with islands or regions of the p-n/n-p structure.

In some embodiments, the structure is a p-n structure.

In some embodiments, the structure is an n-p structure.

The thickness of the p-n/n-p structure is typically in the nanometer scale. The thickness of the p-layer can be varied between 10 to 10,000 nm, depending on desired optical and electrical properties. The thickness of the n-layer can be varied in the same range, yielding combined p-n layer thicknesses of 20 to 20,000 nm. In some embodiments, each of the layers making up the p-n/n-p structure is about 50-100 nm total thickness.

The p-type materials may be selected amongst organic semiconductor pigments, which may or may not be polymeric. Non-limiting examples of such materials include metal containing or metal free phthalocyanine ($H_2Pc$), 2,3-naphthalocyanine, benz[b]anthracene, 5,5''''-Bis(2'''',2''''-dicyanovinyl)-2,2':5',2'':5'',2''':5''',2''''-quinquethiophene, bis(ethylenedithio) tetrathiafulvalene, 2-[(7-{4-[N,N-bis(4-methylphenyl)amino]phenyl}-2,1,3-benzothiadiazol-4-yl)methylene]propanedinitrile, 6,13-bis((triethylsilyl)ethynyl)pentacene, Coronene, dibenzotetrathiafulvalene, 5,5'-Di(4-biphenylyl)-2,2'-bithiophene, 3,3'''-Didodecyl-2,2':5',2'':5''',2'''-quaterthiophene, 5,5'-Dihexyl-2,2'-bithiophene, 3,3'''-dihexyl-2,2':5',2'':5'',2'''-quaterthiophene, 5,5''''-Dihexyl-2,2':5',2'':5'',2''':5''',2''''-sexithiophene, dinaphtho[2,3-b:2',3'-f]thieno[3,2-b]thiophene, 2-[7-(4-diphenylaminophenyl)-2,1,3-benzothiadiazol-4-yl]methylenepropanedinitrile, 2,6-diphenylbenzo[1,2-b:4,5-b']dithiophene, 2,7-diphenyl[1]benzothieno[3,2-b][1]benzothiophene, 6,13-diphenylpentacene, 2-{[7-(5-N,N-ditolylaminothiophen-2-yl)-2,1,3-benzothiadiazol-4-yl]methylene} malononitrile, 2,6-ditolylbenzo[1,2-b:4,5-b']dithiophene, Merocyanine dye, 13,6-N-sulfinylacetamidopentacene, tris[4-(5-dicyanomethylidenemethyl-2-thienyl)phenyl]amine, Rubrene, α-sexithiophene, tetrathiafulvalene, epindolidione, quinacridone, indanthrene, flavanthrone or violanthrone. These layers may be intrinsic (undoped) or may be partially-doped layers.

In some embodiments, the p-type material is a metal containing or metal free phthalocyanine ($H_2Pc$). In some embodiments, the p-type material is metal free $H_2PC$.

The n-type materials may be selected amongst organic semiconductor pigments, that are optionally polymeric. Non-limiting examples of such materials include N,N'-dimethyl perylenetetracarboxylic diimide (PTCDI), N,N'-bis(2,5-di-tert-butylphenyl)-3,4,9,10-perylenedicarboximide, 1,3,6,8(2H,7H)-tetraone, 2,7-dicyclohexylbenzo[lmn][3,8]phenanthroline, 1,3,8,10(2H,9H)-tetraone, 2,9-bis(2-phenylethyl)anthra[2,1,9-def:6,5,10-d'e'f']diisoquinoline, fullerene, 5,10,15,20-Tetrakis(pentafluorophenyl)-21H,23H-porphine, 7,7,8,8-tetracyanoquinodimethane, 2,3,5,6-tetrafluoro-7,7,8,8-tetracyanoquinodimethane, 1,2,3,4,5,6,7,8-octafluoro-9,10-bis[2-(2,4,6-trimethylphenyl)ethynyl]anthracene, 1,2,3,4,5,6,7,8-octafluoro-9,10-bis[4-(trifluoromethyl)phenyl]anthracene, 1,4,5,8-naphthalenetetracarboxylic dianhydride, Indeno[1,2-b]fluorene-6,12-dione, 2,9-dipropylanthra[2,1,9-def:6,5,10-d'e'f']diisoquinoline-1,3,8,10(2H,9H)tetrone, N,N'-dipentyl-3,4,9,10-perylene dicarboximide, 1,3-dimethyl-2-phenyl-2,3-dihydro-1H-benzoimidazole, 4-(2,3-dihydro-1,3-dimethyl-1H-benzimidazol-2-yl)-N,N-dimethylbenzenamine, N,N'-dimethyl-3,4,9,10-perylenedicarboximide, 4-(1,3-dimethyl-2,3-dihydro-1H-benzoimidazol-2-yl)-N,N-diphenylaniline, 2,9-dihexylanthra[2,1,9-def:6,5,10-d'e'f']diisoquinoline-1,3,8,10 (2H,9H)tetrone, 2,7-dihexylbenzo[lmn][3,8]phenanthroline-1,3,6,8(2H,7H)-tetrone, 2,9-diheptylanthra[2,1,9-def:6,5,10-d'e'f']diisoquinoline-1,3,8,10(2H,9H) tetrone, 1,7-dibromo-3,4,9,10-tetracarboxylic acid dianhydride, 6,12-bis(2,4,6-trimethylphenyl) indeno[1,2-b]fluorine, 1,2,3,4,8,9,10,11,15,16,17,18,22,23,24,25-hexadecafluoro-29H,31H-phthalocyanine, 2,2'-bis[4-(trifluoromethyl)phenyl]-5,5'-bithiazole, 5,5'''-bis(tridecafluorohexyl)-2,2':5',2''':5''',2''''-quaterthiophene, N,N'-bis(3-pentyl)perylene-3,4,9,10-bis(dicarboximide), 6,12-bis(2,3,4,5,6-pentafluorophenyl)indeno[1,2-b]fluorine, 2,9-bis[(4-methoxyphenyl)methyl]anthra[2,1,9-def:6,5,10-d'e'f']diisoquinoline-1,3,8,10(2H,9H)tetrone, bisbenzimidazo[2,1-a:2',1'-a']anthra[2,1,9-def:6,5,10-d'e'f']diisoquinoline-10,21-dione, indigo, 6,6'-dibromoindigo (tyrian purple), isoindigo, indanthrone, diindeno[1,2,3-cd:1',d',3'-jk]pyrene, diindeno[1,2,3-de,1',2',3'-kl]anthracene or dinaphth[1,2-a:1',2'-h]anthracene.

In some embodiments, the n-type material is N,N'-dimethyl perylenetetracarboxylic diimide (PTCDI).

The metal layer onto which the p-n/n-p structure is formed is a layer of a metal having a work function which aligns with the conduction band of the p-type material (or n-type material) layer immediately formed thereon, to minimize ohmic loss in hole extraction. The metallic material is selected to be stable in and compatible with physiological conditions. The material must be nontoxic and safe. Where the metal layer is replaced, as disclosed herein, with a layer of a conductive material the same conditions should be met.

In some embodiments, the metal layer is a layer comprising at least one metal selected from Cr, Ti, Au, Al, Zn, W, Cu, Pd and Pt and combinations thereof.

In some embodiments, the metal layer may be replaced with a layer of at least one material selected from stainless steel and TiN, or carbon-based conductors such as carbon black, graphite, graphene, carbon nanotubes. When optical transparency of the metallic layer is desired, materials such as indium tin oxide (ITO), fluorine-doped tin oxide (FTO), or zinc oxide based transparent conductors, and combinations thereof, may be used.

In some cases, the metal layer is replaced with a layer of a conductive polymer(s). Non-limiting examples of such conductive polymers include poly(3,4-ethylenedioxythiophene) (PEDOT), poly(3,4-ethylenedioxythiophene)/polystyrene sulfonate (PEDOT/PSS) and others.

In some embodiments, the metal or conductive material layer is a multilayer, wherein each layer consists of a different metal or conductive material, as disclosed. In some embodiments, each layer comprises at least one metal and/or at least one conductive materials. In some embodiments, the multilayer is a bilayer of two metals or conductive materials, the metal/conductive material being in direct contact with the p-n/n-p structure is selected from Au, Pt and Pd, or is of a material other than a metal, such as carbon nanotubes. The metal or conductive material layer must be also in electrical contact with the physiological medium in which the device operates.

The substrate on which the metal or conductive material film is formed and the device of the invention constructed may be of any inert solid material which may be rigid, flexible or in some cases transparent to light. In some embodiments, the substrate is made of a polymeric or non-polymeric material. Non-limiting examples include polyimide, polystyrene, silk, polysaccharides, cellulose, glass, silicon, aluminium oxide and titanium oxide. The substrate may be a surface region of any solid material which may be substantially thin and flat (2-dimensional) or may be in a 3-dimensional form. The surface may be a surface region or a particle, microparticle or nanoparticle, and the device may thus be in particulate (micro or nano) form.

In some embodiments, the device comprises a surface that only on a portion thereof an active tri-layer of the invention is formed. The active tri-layer may be formed on a single region of the surface or on multiple regions of the surface such that the much larger device surface, most of which being free of the active tri-layer, provides means by which e.g., to fix the device to the vicinity of the tissue to be excited, while the active region(s) are positioned directly on the tissue to be excited.

As stated herein, the device of the invention is a photo-response device; a device that upon exposure to light, at a predetermined wavelength, produces an electrical response or output (e.g., current) that is sufficient for cellular or tissue stimulation. Devices according to the invention are photo-responsive at wavelengths between 400 and 2,000 nm and may be tailored to be responsive at any wavelength range therebetween. In some embodiments, the absorption is optimized in the 650-850 nm region, the tissue transparency window, in order to enable stimulation deep inside tissue or through bone.

The fact that devices of the invention need no wiring or external bias and may be designed to be freestanding and untethered when in operation, reduces mechanical failure, potential movement of the device during operation (with respect to the tissue being stimulated), allows for a better selectivity of excitable tissues or cells and permits production of the device in an endless number of variations and sizes. These advantages improve the functionality, versatility, longevity, biocompatibility and stability of devices of the invention, rendering them safe for medicinal or otherwise any purposive use on humans.

Generally speaking, devices of the invention may be used for stimulating mammalian tissues, or in any therapeutic method requiring tissue stimulation. The "tissue" to be stimulated by a device of the invention may be any cell or collections of cells found within the nervous system and/or the muscles. The cells or tissues may be cells or tissues of any muscle of the body, the brain, the spinal cord, the peripheral nerves or individual organs, at a nerve interface (e.g., the heart, the bladder, the pancreas) or the eye. When the tissues or cells are neurostimulated electricity (e.g., by way of electrical pulses) is delivered to a neuron, a nerve cell, or generally to a target location of the nervous system. The delivery of electricity may excite the nerve cell, and thereby trigger an action potential. The devices of the invention are therefore based on neurostimulation and photo-electro myostimulation as a therapeutic principle and can be used for the treatment and management of a variety of conditions or diseases. Such may be selected from pain, sleep disturbances, Parkinson's disease, epilepsy, hand tremor, myodystonia and retinal dysfunction. Where the tissue or cells to be stimulated are not available for stimulation, such may be brain tissues, the device of the invention may be implanted under the skin or at the site of desired stimulation and configured for operation by an auxiliary light source implanted with the device or by deep-penetrating light (such as NIR).

The tissue may be an exposed tissue or an internal body tissue such as the spinal cord and deep brain tissues. As the device may be a self-standing device that requires no bias, it is not limited in shape, structure and size and thus may be adapted or tailored to meet any one particular or generic application and site of operation. For example, implantable devices may take on the shape of a thin film, micro or nanoparticles; and devices for external use may be in the form of a patch, a self-adhering ultrathin device and/or a device with a built-in illumination source for selecting a desired wavelength. Implantable devices may be irradiated with light of longer wavelengths that can penetrate a tissue much deeper than visible light. Thus, near-infrared lasers or LEDs placed on the surface of the skin or subcutaneously may be used to transmit photons.

Additionally, devices according to the invention may be implemented as wearable devices that can be worn on a body region, wherein at least a portion of the wearable device is a photoresponsive feature according to the invention.

A device may be implanted or positioned (in case it is placed on an exposed tissue surface) at or proximate to specific nerves or portions of nerves identified to control or transmit the nerve pulses that trigger the function which the system is aimed at stimulating. Depending on the size and/or shape of the device, the device may be implanted in the vicinity of dendrites, synapses, axons, or axon terminals.

A photoresponse occurs when light with wavelengths between 400 nm and 2,000 nm is projected onto a tissue in the direction of the device or from any direction towards the device itself or the vicinity thereof, by any illumination means available. For certain applications, the device may be used in conjunction with a micro-waveguide capable of directing light to the device to thereby produce the photo-response effect, stimulating the tissue.

The characteristics of the electrical pulses generated by illumination may be defined by, for example, a pulse width or pulse duration, a pulse amplitude or power, a pulse frequency, and a pulse shape or waveform, and the illumination may be adjusted or configured to provide a modulated set of electrical pulses. Modulating the electrical pulses may include adjusting the different variables continuously or at discrete intervals. Light pulse duration is varied between 1 is to hundreds of ms, depending on the desired application. Very short pulses can lead to rapid and partial depolarization, while longer pulses can lead to complete depolarization. Pulses longer than 10 ms may also lead to photothermal heating effects, which may be desired in some cases. Modulating the pulse period to 1 ms or less can lead to a quasi-steady state where the region around the photocapacitor is permanently depolarized, since cell membranes cannot capacitively relax fast enough.

Thus, the invention further provides a device for stimulating a mammalian tissue, the device being a photoresponse device according to the invention. In some embodiments, the device is engineered or configured to operate under physiological conditions, e.g., when placed in said tissue (or in an intercellular fluid in vicinity of mammalian cells to be stimulated).

The invention further provides a method for stimulating an excitable tissue or cells, the method comprising placing or positioning into, onto or in the vicinity of a target excitable tissue or cells at least one photoresponse device according to the invention; and focusing light with a wavelength between 400-2,000 nanometers onto the device, to thereby cause a photoresponse effect (electrical pulse), as explained herein, and stimulation of the excitable tissue or cells.

The invention further provides a method of generating an electrical pulse at the vicinity of a biological tissue or cells, the method comprising positioning into, onto or in the vicinity of a target excitable tissue or cells at least one photoresponse device according to the invention; and focusing light with a wavelength between 400-2,000 nanometers onto the device, to thereby generate an electrical pulse.

A device according to the invention may be positioned (placed, inserted, adhered to, associated with a tissue or cells to be excited) by implantation in a body region or cavity or by a syringe or a cannula or by minimally invasive procedures or during a surgical procedure. Alternatively, a device may be placed onto a tissue surface or in the vicinity of the tissue. Where the device is larger than the surface, e.g., tissue, to be stimulated, the active tri-layer is ideally positioned on or in the vicinity of the tissue to be stimulated to achieve effective stimulation.

The invention further provides a retinal implant being a device according to the invention.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 1A-E depict exemplary organic photocapacitor devices according to the invention: FIG. 1A is a schematic representation of a photocapacitor device consisting of sequentially deposited Cr/Au and $H_2Pc$ (p-type) and PTCDI (n-type) layers. FIG. 1B shows the molecular structures of the pigment semiconductors. Metal-free phthalocyanine ($H_2Pc$) functions as the primary light-absorbing layer and p-type electron donor, while N,N'-dimethyl perylenetetracarboxylic diimide (PTCDI) acts as the n-type electron-acceptor, which attains a negatively-charged surface upon illumination. FIG. 1C is anenergy band illustration of a metal-p-n photocapacitor device during the start of the illumination pulse when the capacitor charges. FIG. 1D is a two-dimensional slice of an electrostatic simulation of electrical potential distribution in electrolytic solution above a metal-p-n photocapacitor, when the p-n junction is charged to 250 mV. The positive potential is closely localized on the exposed metal film, while a negative potential 'plume' extends from the top of the p-n heterojunction layer. Scale bar=200 m. FIG. 1E presents the mechanism of capacitive coupling of an illuminated photocapacitor with an adjacent cell.

FIG. 2A presents a two photocapacitor measurement configurations for Type I samples (1×1 cm² p-n area on a 1.5×1.5 cm² gold coated glass slide): Grounded metal samples for voltage (V) and current (I) measurements, and "floating samples" for voltage transient (Vt) measurements. Numbers denote which figure panels show measurements in the given configuration. FIG. 2B shows the optical absorbance overlaid with spectral responsivity of Type I photocapacitors. FIG. 2C provides photoelectric characterization. c1 and c2 are photovoltage (V) and photocurrent (I), respectively, measured between the bath electrode and the grounded p-n-metal device. c3 is the photovoltage transient (Vt) measured 10 μm above the p-n film, using a glass capillary electrode versus bath reference electrode. Vertical grey lines indicate onset and termination of the light pulses. FIG. 2D provides cathodic peak value of Vt (cpVt) is a function of peak anodic current divided by the spot size radius $r_{(spot)}$. FIG. 2E shows cpVt as a function of illumination intensity for two different electrolytes: phosphate-buffered saline (PBS) and artificial cerebrospinal fluid (aCSF). FIG. 2F presents a lateral profile of cpVt measured 10 m above the surface for two different light spots that are significantly smaller than the p-n region. Measurements start from the center of the light spot and are measured laterally at 25 m increments. Cathodic charging is strongest in the center of the spot, with Vt rapidly decaying outside of the directly illuminated region. FIG. 2G, Stress test results on grounded samples to evaluate the effects of different sterilization procedures. Measurement was done after sequential: oxygen plasma, triple treatment with absolute ethanol, storing overnight in buffer, UV sterilization, and second triple treatment with absolute ethanol.

FIGS. 3A-D depicts photostimulation of neuronal cultures. FIG. 3A, Cortical primary neurons cultured on PDL-coated petri-dishes, control sample (n=4). Scale bar=100 μm. FIG. 3B, Cortical primary neurons cultured on type I devices (n=3). FIG. 3C, Calcium imaging traces (dF/F) of neurons cultured on PDL coated petridish. FIG. 3D, Ca imaging traces of neurons cultured on type I devices. Vertical red lines in (c) and (d) indicate a light stimulation of 100 consequative pulses (600 nm, 480 mW/cm², pulse duration 5 ms, interpulse interval 10 ms).

FIG. 4A, Type II samples comprise p-n circular islands of varying size deposited on an "infinitely large" gold layer. Type III are devices where the size of both p-n islands and the underlying metal is varied. Scale bar below the pigment image=500 μm. FIG. 4B, The effect of p-n island size. Cathodic peak values of voltage transients (cpVt) from type II samples as a function of p-n island size for three different illumination intensities. Vt is measured 10 μm above the centre of the p-n islands. Light spot size is larger than the maximal island size. FIG. 4C. Lateral cpVt profile measured 10 μm above a type III sample, showing the maximum value of Vt in the centre of the p-n island, with voltage changing sign above the metal film. Measurements are from the centre of the p-n island and moving aside at 25 μm increments. FIG. 4D, The effect of gold size on Vt measured 10 μm above the p-n film in type III samples with constant p-n island size and variable metal size. FIG. 4E and FIG. 4F. p-n circular islands of varying size deposited in between the electrodes of multielectrode arrays (MEA) with either "infinitely large" (e) or ⌀=480 μm of circular (f) gold layer. Scale bars=1 mm.

FIG. 5A, A piece of light insensitive embryonic chick retina was laid on the MEA shown in FIG. 4E. Light pulses illuminated only a pigment bilayer of 100 μm marked by a red arrow using 40× objective. Electrical stimulation injected to electrode G4, marked by a blue arrow. Direct responses of the retinal ganglion cells (RGC) were detected only in red-circled electrodes for light stimulation and blue-circled electrodes for electrical stimulation. Corresponding regression lines for these electrodes are shown and their linear equation, with a slope of 38°. FIG. 5B, An image of a retina placed on the MEA, with optical focus on the photoreceptor nuclear layer. The p-n island (marked with square in FIG. 5A) is clearly visible beneath the retina. FIG. 5C, The same image as in FIG. 5B focused on the nerve fibre layer. The orientation of the fibres is clearly seen in the image, found to be 38° by the FFT directionality histogram. FIG. 5D, Current pulse stimulation of the retina. Relative location of the injected electrode, G4, is marked by a blue arrow and circle. The latency of the response is increased when recorded from more distant electrodes to the stimulating electrode. This measurement serves as an internal control. FIG. 5E, Photostimulation of the retina. Relative location of the illuminated pigment is marked by a red arrow and circle. Electrodes $H_4$ and G5, which are close to the source, record the electrical response of the pigment bilayer as well. These responses are seen in the overlaid red traces, recorded from pulses that did not evoke retinal responses. FIG. 5F. Direct responses to 5 ms light pulse of different intensities showing the intensity-response dependence. Vertical grey lines indicate onset and termination of the light pulses.

FIG. 8A, Transient voltages, Vt, measured with a glass capillary electrode placed above a 30 μm diameter MEA electrode (left inset) at 4 different distances. Biphasic current pulse of 5 uA, 300 is (0.2 mC/cm$^2$, right inset) were injected into the MEA electrode. FIG. 8B, Cathodic peak of the transient voltages as a function of the injected current measured at four different distances above the MEA electrode. The equivalent charge density is shown above.

FIGS. 10A-D show photothermal response of Cr/Au-H$_2$Pc/PTCDI filn FIG. 10A, Calibration procedure by measuring electrode resistance as a function of bath temperature. Electrode resistance was calculated by measuring the electrode voltage drop during 10 nA current injection. FIG. 10B1-B4 and FIG. 10C1-C4 are the same traces, respectively, at different time and voltage scales. Sample was illuminated by a 660 nm LED, either continuously for 1.5 s (B1,2., C1,2) or 100 pulses of 5 ms, 10 ms interval (B3,4., C3,4). Intensity was either 1700 mW/cm$^2$ (B1-3., C1-3) or 480 mw/cm$^2$ (B4., C4: similar to the cell culture activation protocol, see FIG. 3). Electrode was either unbiased (B1., C1) or biased by 10 nA (B2-4., C2-4). The latter resulted in a voltage drop proportional to the electrode resistance at a bath temperature of 36.8° C., which was set to zero before illumination. Light pulses resulted in transient voltage changes typical to the photoelectrical response. Biased measurements also show a DC component that is proportional to the change in electrode resistance due to photothermal heat dissipation. Changes in temperature were calculated according to the calibration procedure in FIG. 10A: ΔV1=−0.6 mv, ΔV2=−0.5 mv, ΔV3=−0.2 mv. These corresponds to ΔT1=0.83° C., ΔT2=0.69° C., and ΔT3=0.28° C. FIG. 10D, Characteristic photothermal response for 1.5 s constant illumination of 1700 mW/cm$^2$ (as in B2, C2).

DETAILED DESCRIPTION OF EMBODIMENTS

Materials

Figure 1D:
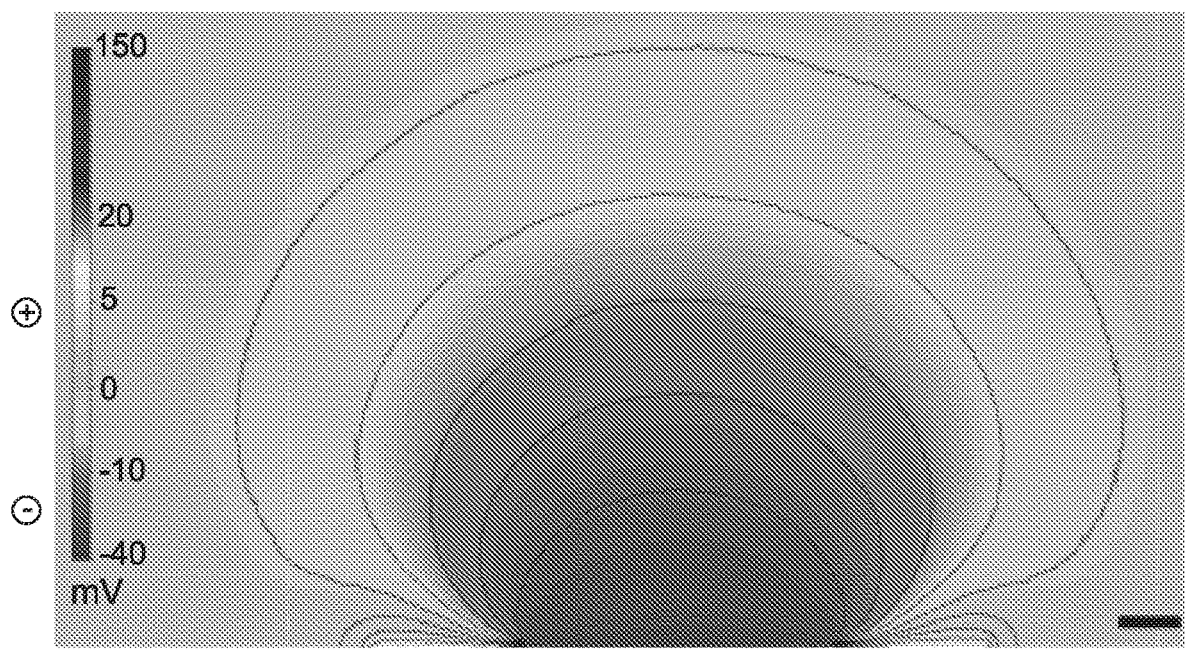

Phthalocyanine H$_2$Pc (Alfa Aesar), ZnPc (BASF) and CuPc (BASF) were each purified by three-fold temperature gradient sublimation in a vacuum of <1×10$^{-3}$ torr. PTCDI, N,N'-Dimethyl-3,4,9,10-perylenetetracarboxylic Diimide (BASF), was likewise purified thrice by sublimation.

Device Fabrication

Photocapacitor devices were fabricated using physical vapour deposition processes either on clean microscope slide glass or on commercial multielectrode arrays (Multi-channel Systems GmbH), with both metal and organic regions defined by stainless steel shadow masks. Both glass and MEA substrates, after solvent cleaning, were treated with UV-generated ozone and a layer of chromium (2 nm) followed by gold (18 nm) was evaporated at a base pressure of <1×10$^{-6}$ mbar at a rate of 0.2 Å/s and 3-5 Å/s, respectively. It is known that following these fabrication procedures gives primarily Cr$_2$O$_3$ rather than metallic Cr. Following evaporation, the samples were exposed to UV-generated ozone for 15 minutes and then placed into a chamber held at 75° C. containing vapour of n-octyltriethoxysilane (OTS) for 2 hr. Following OTS treatment the substrates were rinsed with acetone and water and placed in boiling acetone for 15 minutes to remove multilayers and excess silanisation physioadsorbed on the Cr/Au or TiN electrodes (the latter in the case of MEA). The OTS layer was found to improve the adhesion of the organic semiconductor layer and prevent delamination, and produced reliably higher photovoltage than bare Cr/Au. Following rinsing with isopropanol and water and drying under a nitrogen stream, the samples were placed with appropriate shadow masking in an organic materials evaporator. The pigment layers were evaporated at a rate of 0.5 Å/s for the p-type layer and 5-6 Å/s for the n-type at a base pressure of <1×10$^{-6}$ mbar, to give a total thickness of 60 nm consisting of 30 nm of p- and n-type.

Photo-Response Characterization

The illumination unit consisted of a light-emitting diode (LED) with a peak wavelength of 660 nm (Thorlabs) mounted on an Olympus upright microscope (BX51WI) using a 4× or water immersion objectives of 10, 20, and 40×, resulting in illumination intensities within the range of 0.6-1725 mW/cm$^2$. The measurement unit consisted of a current amplifier (model 1212; DL Instruments) or voltage amplifier (model ELC-03XS, npi electronic GmbH). A photogenerated voltage was measured between the underlying metal electrode and a reference electrode (either Au or Ag/AgCl) in phosphate buffered saline (PBS) or modified Tyrode's solution (5 mM KCl, 25 mM NaHCO$_3$, 10 mM glucose, 1.2 mM MgSO$_4$, 1.2 mM HEPES, 0.5 mM glutamine, 2.5 mM CaCl$_2$). Voltage transients were recorded using a micropipette electrode filled with 3M KCl, mounted on a computer motorized micromanipulator (model Patch-Star, Scientifica) vs. Ag/AgCl reference electrode in the electrolyte.

A Xenon-Discharge Lamp and Czerny-Turner Monochromator were used as light source to acquire the photocurrent spectra. The photocurrents were amplified using a Lock-in amplifier and chopper operated at 29 Hz. The current rms values were acquired as a function of wavelength and normalized for the light intensity as measured with a pyroelectric detector. Impedance spectra were acquired in 0.1 M KCl with a Metro-Ohm PGSTAT 204 at OCP conditions.

Electrostatic Modeling

Electric potential distribution of the device immersed in electrolyte was modeled using the Robin Hood Solver software package for complex 3D electrostatic problems using the Robin Hood calculation method. Charged photocapacitor devices were modeled as two concentric metal plates—larger bottom gold electrode fixed at 0V potential, and the smaller top electrode which represented an equipotential surface at the top of the p-n junction, and which could be set at arbitrary potentials depending on the modeled electrode. The electrodes in the model were separated by a thin dielectric layer with relative permittivity of 3, characteristic to the organic semiconductors used here. The dielectric layer in the model represented the p-n junction region of the device. The space surrounding the device was modeled as a dielectric with relative permittivity of 80.1, representing a water-based electrolyte. All the dimensions in the model were true to the experimentally measured devices.

Neural Culture

All mice were treated in accordance with the principles and procedures of the Israel National Institute of Health and the United States National Institutes of Health (NIH) Guidelines for the Care and Use of Laboratory Animals. Protocols were approved by the Institutional Animal Care and Use Committee of the Tel Aviv University. Dissociated cortical cultures were prepared as follows: the entire cortices of SV129-mice, post-natal 0-1, were removed. Cortical tissue was digested with 0.065% trypsin (Biological Industries) in PBS for 15 min, followed by mechanical dissociation by trituration. Cells were re-suspended in a modified essential medium (MEM) without phenol red and glutamine, 5% horse serum, 50 mM glutamine, 0.02 mM glucose, 0.5% Pen-Strep, 2% B-27, and 0.75% glutamax (Gibco) and plated on either poly-D-lysine (PDL, Sigma) covered petri dish (control) or on type I samples (experiment) with a cell density of 3000 cells/mm$^2$ (~700×10$^3$ cells per dish). Cultures were maintained at 37° C. with 5% $CO_2$. Growth medium was partially replaced every 3-4 days. At 4 DIV, cultures were infected with AAV-CAG-GCaMP6s viral vector (prepared by the Tel Aviv University vector core facility).

Optical Recording Via Calcium Imaging

Calcium imaging recordings were performed on 14 DIV in buffered mice artificial cerebrospinal solution (mice aCSF: 10 mM HEPES, 4 mM KCl, 1.5 mM $CaCl_2$, 0.75 mM $MgCl2$, 139 mM NaCl, 10 mM D-glucose, adjusted with sucrose to an osmolarity of 325 mOsm, and with NaOH to a pH of 7.4). Images were acquired with an EMCCD camera (Andor Ixon-885) mounted on an Olympus upright microscope (BX51WI) using a 20× water immersion objective (Olympus, LUMPLFL NA 0.4).

Fluorescent excitation was provided via a 120 W mercury lamp (EXFO x-cite 120PC) coupled to a GFP filter cube (Chroma T495LP). Images were acquired at 59 fps in 2×2 binning mode using Andor software data-acquisition card (SOLIS) installed on a personal computer, spooled to a high capacity hard drive and stored as uncompressed multi-page tiff file libraries.

Electrical Recordings from Retinas

Coupling between the tissue and the electrodes was improved by placing a small piece of polyester membrane filter (5 µm pores; Sterlitech) and a ring weight on the retina. The filter was removed before light stimulation to minimize scattering. Retinas were kept at physiological conditions, at a temperature of 34° C., and perfused (2-5 mL/min) with oxygenated (95% $O_2$, 5% $CO_2$) chick aCSF solution (5 mM KCl, 25 mM $NaHCO_3$, 9 mM glucose, 1.2 mM $MgSO_4$, 1.2 mM HEPES, 0.5 mM glutamine, 2.5 mM $CaCl_2$). Neuronal signals were amplified (gain ×1100 MEA1060-UP; Multi-Channel Systems), digitized using a 64-channel analogue to digital converter (MC_Card; MultiChannel Systems), and recorded (MC_Rack; MultiChannel Systems). Direct retinal responses were recorded with 30-µm diameter TiN electrode MEAs, using electrical stimuli generated by an external stimulator. In vitro epiretinal stimulation was carried out using a biphasic pulse of 300 s and found a critical threshold for eliciting retinal responses of 0.4-1.4 mC/cm$^2$, similar to what has been reported in the literature.

Organic Electrolytic Photocapacitors

Figure 1E:
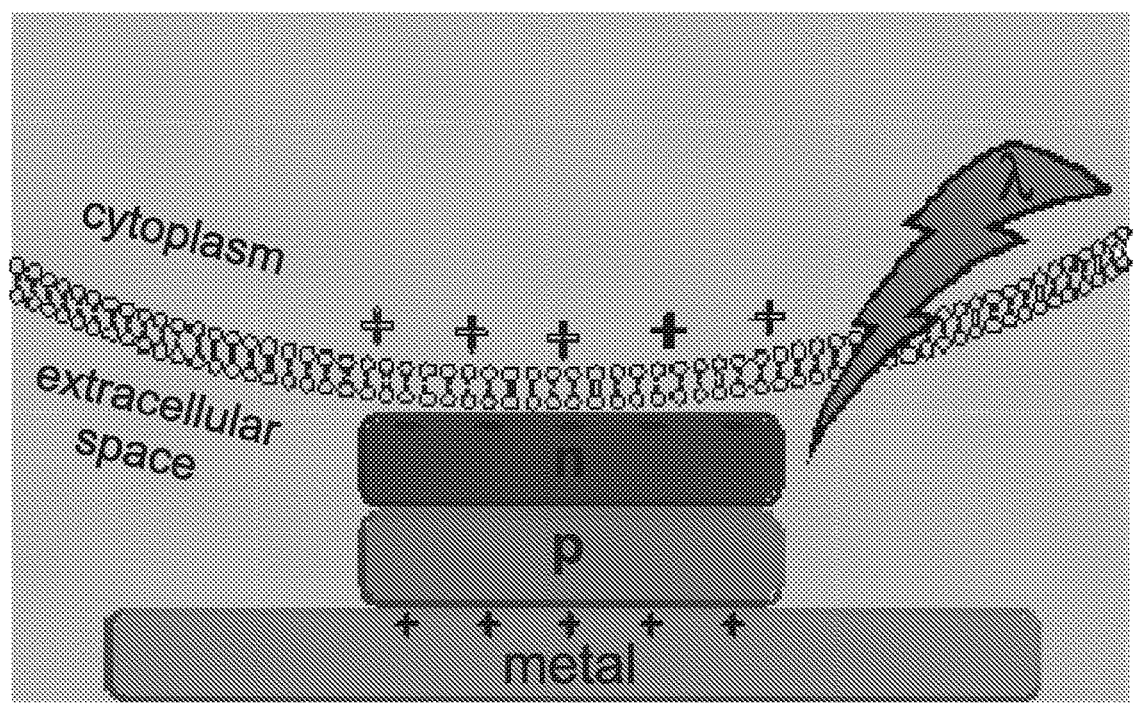
Figure 6A:
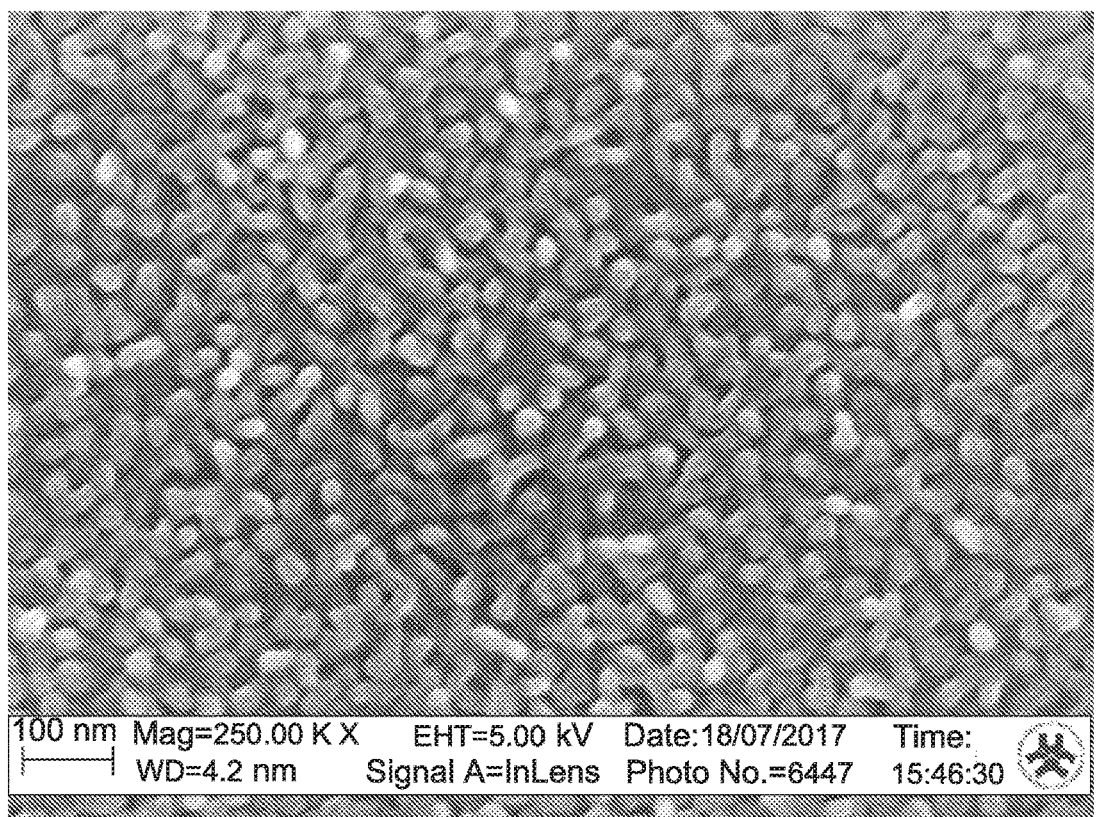
FIGS. 6A-B show scanning electron micrographs of Cr/Au/H$_2$Pc/PTCDI (1/9/30/30 nm) device layers, showing the rough nanocrystalline morphology of the evaporated organic p-n layers at two different magnifications.
Figure 6B:
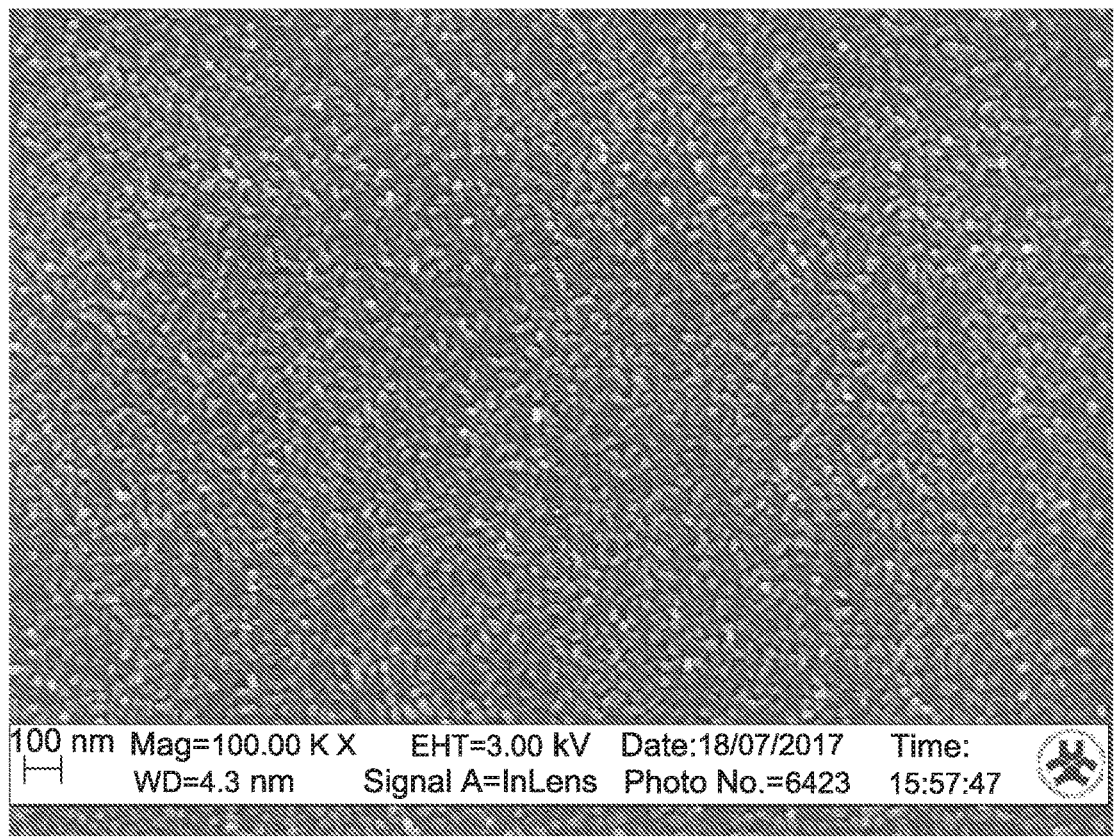
Figure 7A:
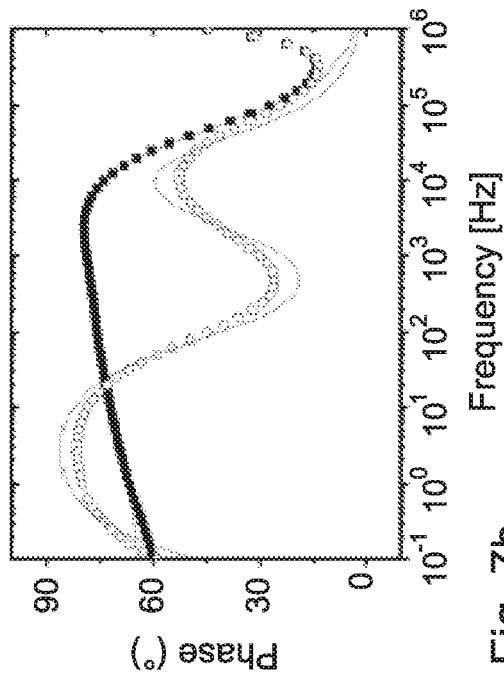
FIGS. 7A-D show the ability using electrochemical impedance spectroscopy (EIS) to calculate resistances and capacitances of the photocapacitor/electrolyte system. The upper panels show Bode plots (left FIG. 7A and right FIG. 7B) for p-n devices measured in dark (black squares) and illuminated (open circles), with lines showing fits to the equivalent circuit diagrams plotted below (top FIG. 7C and bottom FIG. 7D).
Figure 7B:
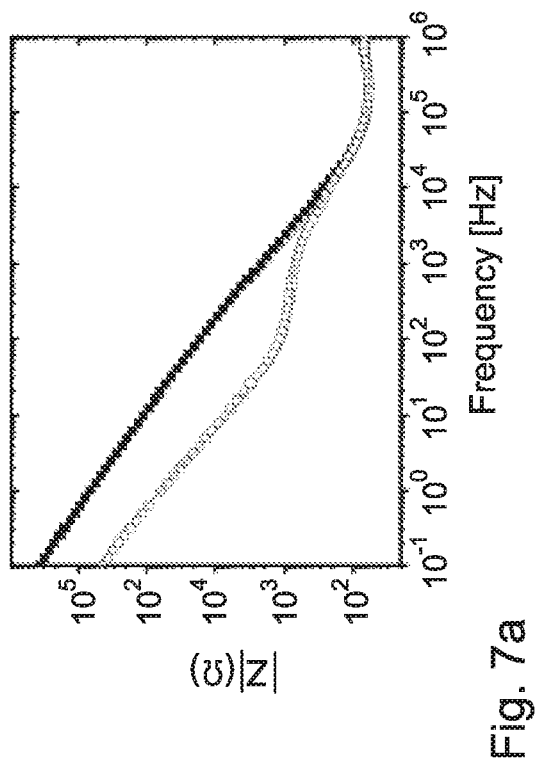
Figure 7C:
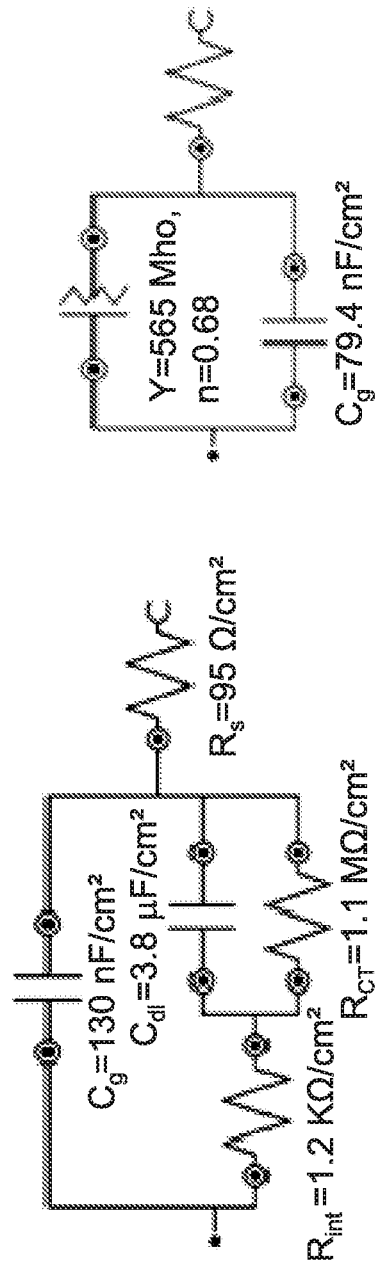
Figure 7D:
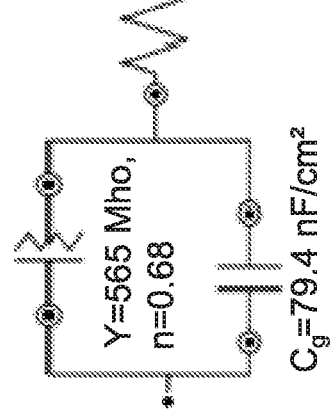

The organic thin film electrolytic capacitor we introduce here is a photodiode which produces electrical double layers upon illumination in water (FIG. 1A). It is believed that the electrical potential difference induced in the surrounding electrolyte could affect the membrane potential of cells in the vicinity, even stimulating action potentials in excitable cells providing the voltage perturbation is large enough. The photocapacitors consist of a p-n heterojunction bilayer on top of a metallic back-contact. A surrounding physiological electrolyte is in contact with both the bottom metal and the top of the p-n junction (FIGS. 1A-C). Devices are fabricated by sequential physical vapour deposition through stencil masks, allowing control over geometries and compatibility with various substrates. In contrast to many semiconductor materials that are sensitive to water, hydrogen-bonded pigments are exceedingly stable in aqueous environments: they can be readily biofunctionalized using simple water-based chemistry and have recently been shown to be stable photoelectrocatalysts in a pH range from 1 to 12. The materials combination which emerged as most promising and was used throughout this study comprises a Cr/Au layer (2 nm/18 nm) followed by a 30 nm layer of metal-free phthalocyanine ($H_2Pc$) and 30 nm layer of N,N'-dimethyl Perylene-3,4:9,10-tetracarboxylic Bisimide, PTCDI for short (FIGS. 1A-B). In an aqueous electrolyte, the device band diagram (shown at the beginning of the light pulse in FIG. 1C) is that of a p-n donor-acceptor photodiode with the metal and the electrolyte forming the bottom and upper electrodes. Photogenerated excitons separate into free carriers at the donor-acceptor (p-n) interface. The electrons accumulate in the n-type semiconducting layer and give rise to an oppositely charged double layer at the semiconductor-liquid interface. Photogenerated holes are injected into the metal, and form an electrical double-layer with the surrounding electrolyte. The maximum possible photovoltage ($U_{photo}$) is given by the difference between the quasi-Fermi level at equilibrium and the conduction band edge of the n-type material. To understand the electrical potential in the surrounding aqueous environment, it is convenient to use electrostatic models. The charge and potential distribution were calculated for different charging voltages. The resultant distribution of electrical potential around a concentric photocapacitor device is plotted in FIG. 1D. Perturbation of the potential has a magnitude of several tens of mV at tens of m above the surface of the p-n layer. Therefore, the photoinduced voltage that a cell in close contact with the photocapacitor will "feel" can in principle be large enough to directly induce action potential generation, via the capacitive coupling mechanism as shown in FIG. 1E. The choice of p-n, as opposed to n-p, gives a negative surface potential on the top of the organic layer, thereby leading to depolarization, as opposed to hyperpolarization, of the attached cell membrane. A further critical aspect of successful device design is the surface morphology of the p-n layer. Nanoscale structure allows for higher photocharge densities to be achieved. Scanning electron microscopy revealed that 60 nm-thick p-n layers have a rough truncated nanopillar-like morphology (FIG. 6A-B) with relatively high surface area.

Figure 2A:
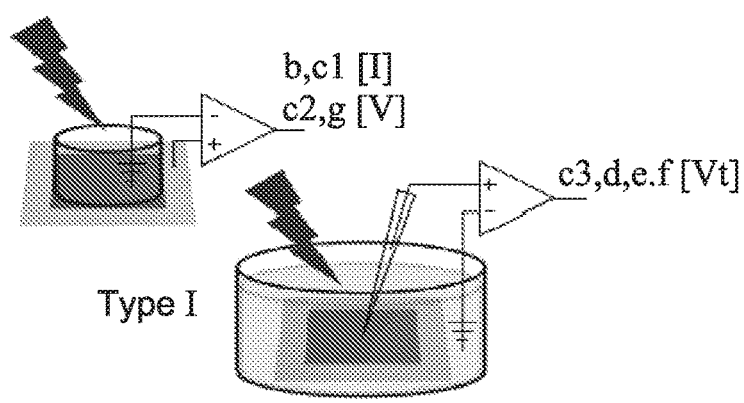
FIGS. 2A-G depict photocapacitive charging of Cr/Au/$H_2Pc$/PTCDI film type I.
Figure 2B:
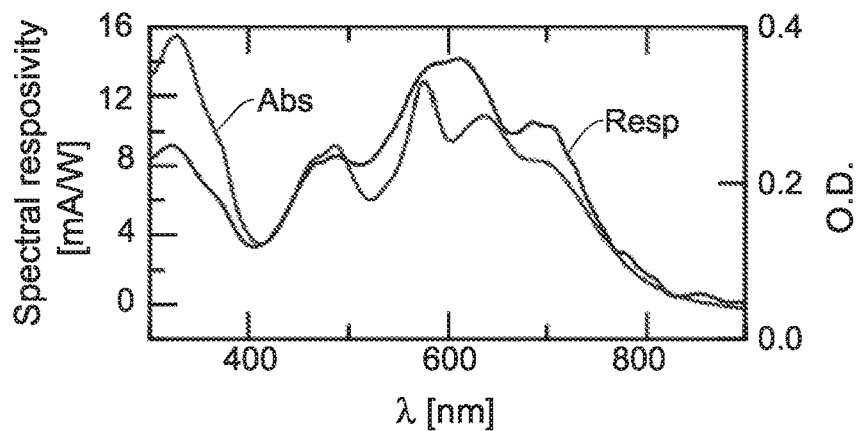
Figure 2C:
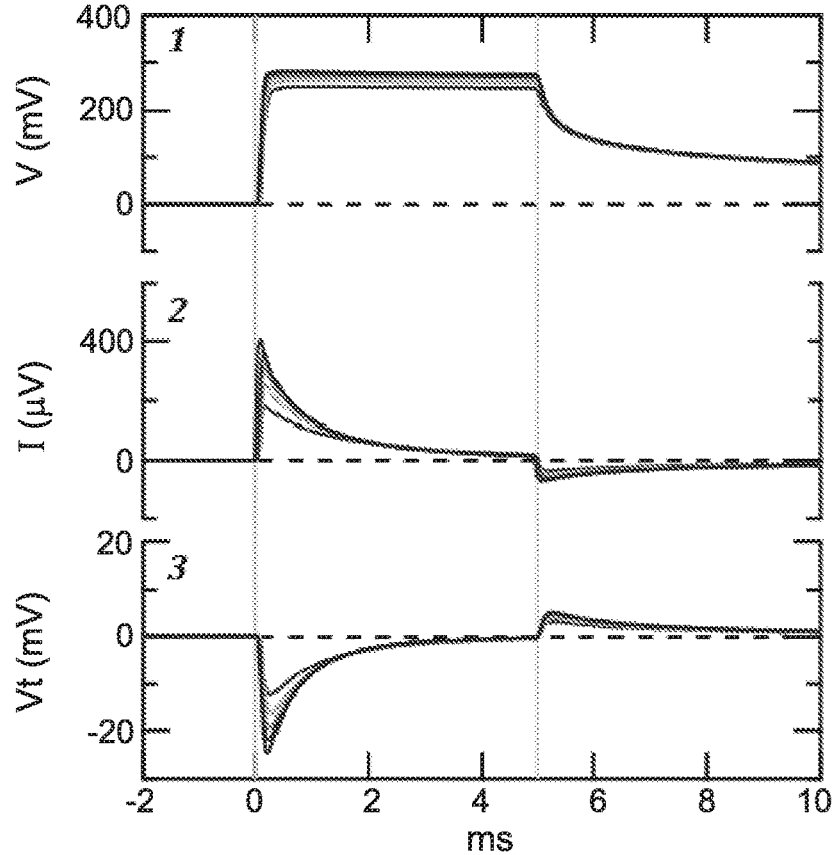

For photocapacitor characterization, we first fabricated 1.5×1.5 cm metallized (Cr/Au) glass slides with 1 cm$^2$ square p-n layer (denoted as type I samples). This arrangement was used to establish baseline parameters for photovoltage/photocurrent, spectral response, and stability. The gold electrode was wired to be grounded or floating (FIG. 2A). The spectral responsivity for photocathodic current was measured for grounded samples, showing strong photocapacitive current generation in the red region of the visible spectrum, 700-600 nm, correlating closely with optical absorbance of the p-n stack (FIG. 2B). FIG. 2C shows photovoltage (V, trace 1) and photocurrent (I, trace 2) values of the photocapacitors measured between the Cr/Au layer versus reference electrode (Ag/AgCl) immersed in the solution, using pulsed illumination (5 ms, 660 nm). These results provide benchmark values for the photovoltages that the bilayer device can generate—around 280 mV (FIG. 2C, trace 1). Corresponding displacement current values, I, are 400 µA/cm$^2$ for light intensities of 60 mW/cm$^2$ (FIG. 2C, trace 2). The photocurrent profile has a capacitive transient shape, and by integrating charge of cathodic (charging) and anodic (discharging) phases, we obtain an equal value of charge, evidencing that the current is non-Faradaic in nature. We obtained more details on Type I devices using electrochemical impedance spectroscopy (EIS). In the dark, the p-n junction response is described by a geometric capacitance of 130 nF/cm$^2$ that corresponds well to the layer thickness of the depleted n-type semiconductor (d=Eε$_0$/C$_g$=33 nm with E=3). Under illumination (620 nm, 0.81 mW/cm$^2$) the impedance drops as carriers are accumulated in the semiconducting layers. The EIS data allows us, on the basis of an equivalent circuit model (FIG. 7A-D), to extract the capacitance between the p-n layer and water (C$_{dl}$=3.8 µF/cm$^2$) and the internal resistance of the illuminated p-n junction (R$_{int}$=1.2 kΩ/cm$^2$). The resistance in the dark, meanwhile, is very high (GΩ/cm$^2$) since both p and n materials are intrinsic semiconductors. Photofaradaic processes that follow a purely resistive path through the junction have only a very small contribution in the impedance spectra and show charge-transfer resistances in darkness or under illumination of R$_{CT}$>1.1 MΩ/cm$^2$, evidencing that the photocurrent is indeed capacitive in nature.

Figure 2E:
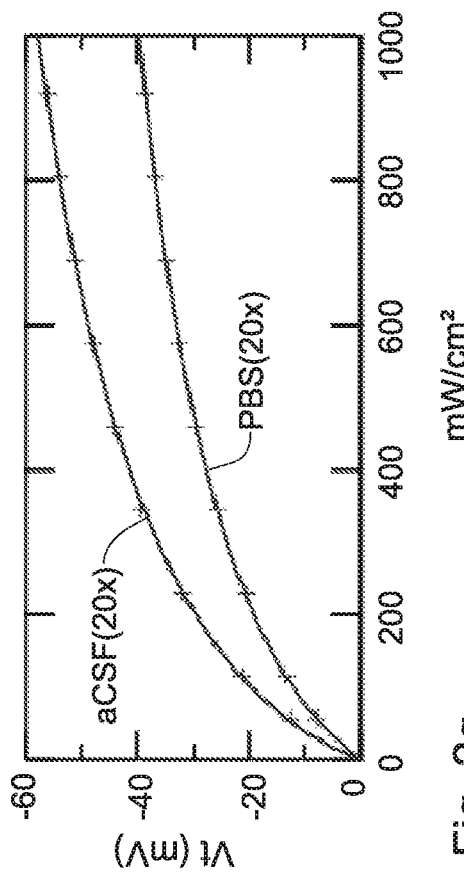
Figure 2G:
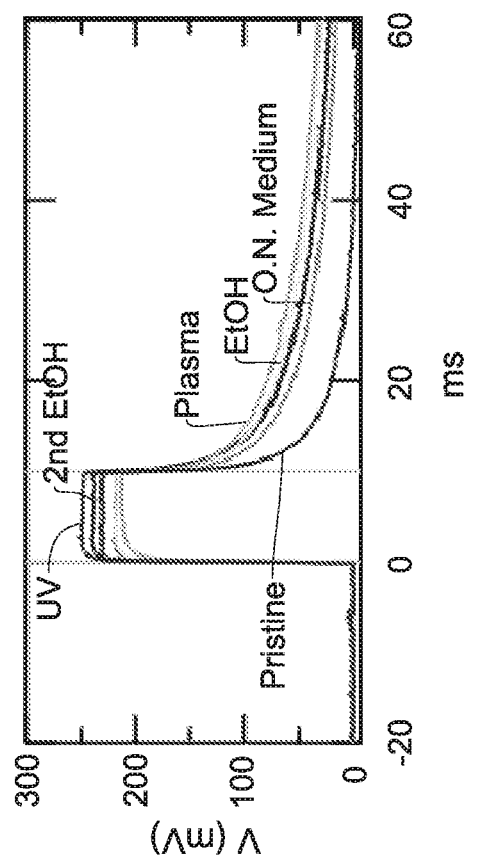
Figure 2D:
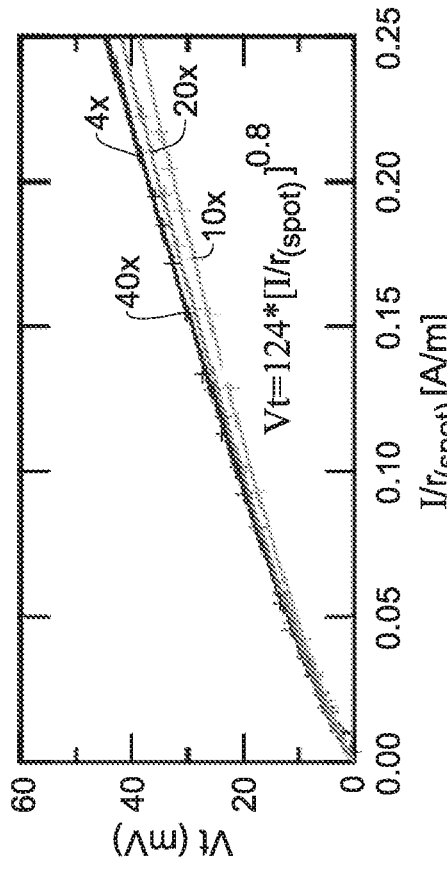
Figure 2F:
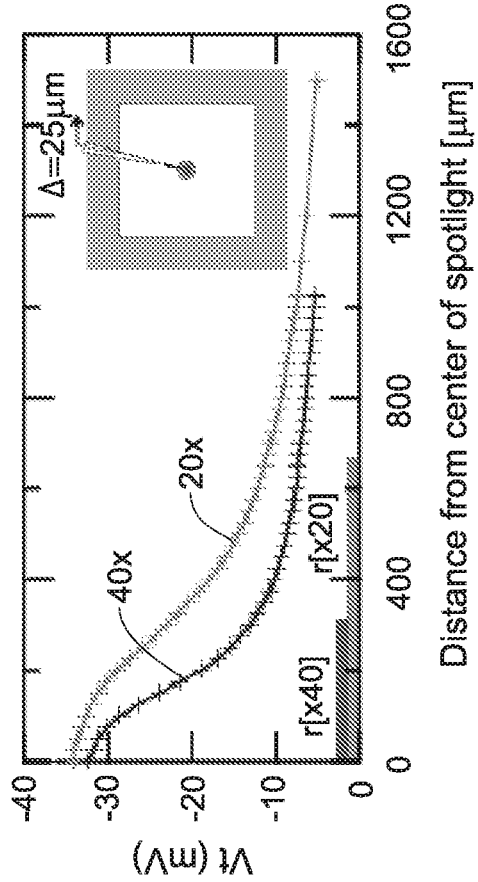
Figure 8A:
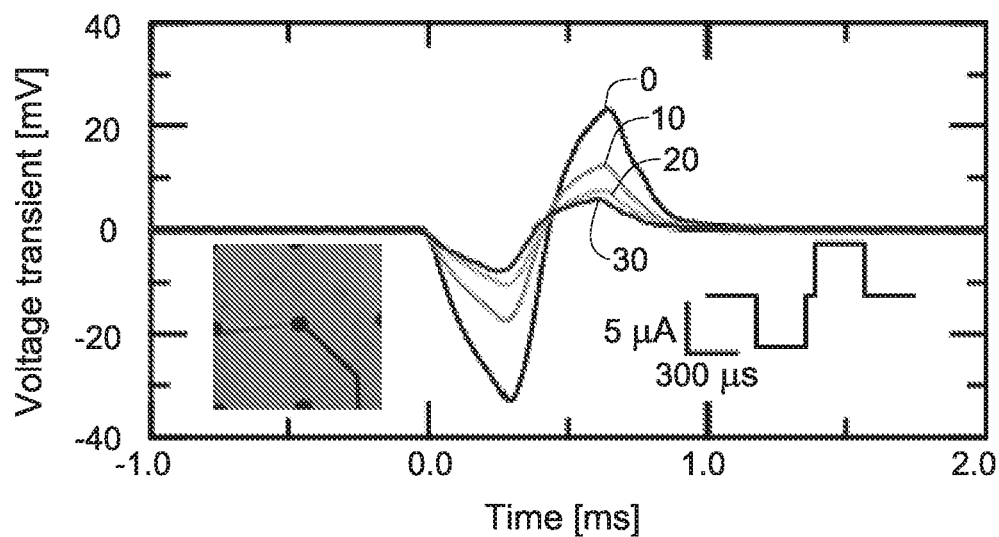
FIGS. 8A-B show MEA current injection voltage transients.
Figure 8B:
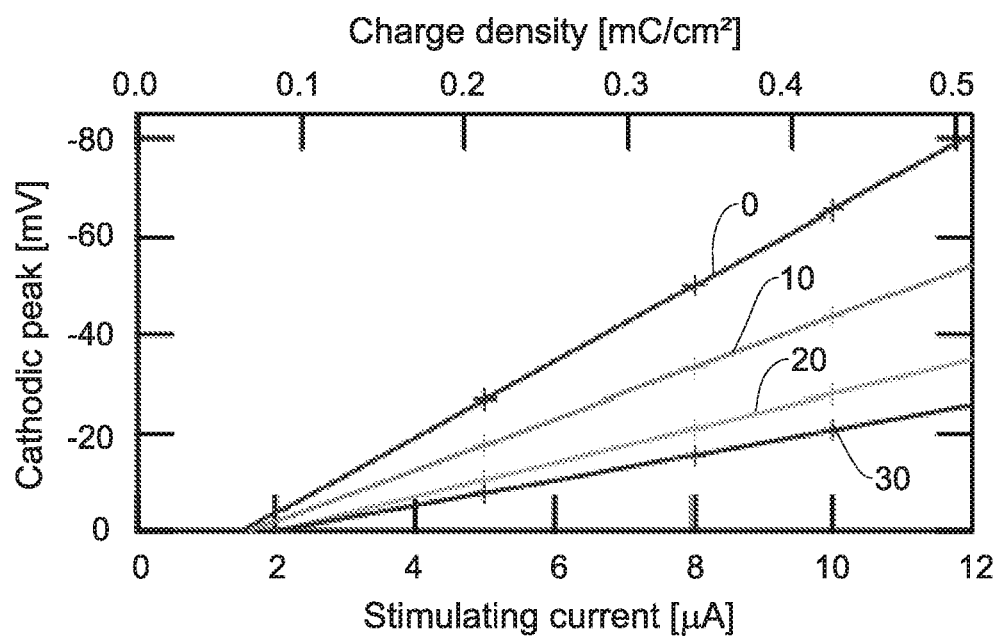

The photovoltage build-up created in solution was next studied above the photocapacitor, this parameter being defined as the transient voltage, V$_t$. This is measured with a glass micropipette electrode in solution mounted on a micromanipulator. All measurements were taken with the micropipette tip 10 m above the pigment surface, versus a large Ag/AgCl bath reference electrode, to give a realistic impression of what voltage perturbations cells adhered to the devices will encounter (FIG. 2C, trace 3). These V$_t$ measurements are taken without the Cr/Au metal film being electrically grounded, the metal is instead in direct contact with electrolyte, allowing us to characterize the operation of the photocapacitors in a wireless, free-standing mode. This scenario reflects the working conditions of standalone implantable device. The measured electrical potential is in the order of a few millivolts, up to 25 mV (to be contrasted with 280 mV under the same illumination conditions when measuring the grounded sample—FIG. 2C, trace 1). Vt profile and intensity is positively correlated with current profile (FIG. 2C, trace 2). It was found that cathodic peak values of Vt (cpVt) are a function of peak anodic current divided by the spot size radius, r$_{(spot)}$, consistent with classic electrostatics for potential above a disk of charge (FIG. 2D). Thus, while a displacement current can be readily associated with a known injected charge value, V$_t$ can also be associated with a corresponding charge value. To empirically link between V$_t$ and electrophysiology-relevant charge injection values we recorded V$_t$ as a function of distance (0-30 µm) from a standard TiN MEA electrode, during stimulation with known current values (using values above the critical threshold needed to achieve action potential stimulation in explanted retinas, ~0.1 mC/cm$^2$), (FIG. 8A-B). The same experiment was repeated, this time recording the photogenerated potentials at 10 µm above the pigment as a function of light intensity, using 10 ms pulses. Photovoltage values were recorded in both phosphate-buffered saline (PBS) and artificial cerebrospinal fluid (aCSF), which mimics the electrolytic environment in the eye. The peak values (cathodic phase) are plotted in FIG. 2E, which shows that photovoltages suitable for direct retinal stimulation can be generated already with illumination values around 100 mW/cm$^2$. We found that measuring type I samples while illuminating a limited area (through ×20 and ×40 objective), the photocathodic voltage is highest in the middle of the illumination spot and decays rapidly at the edges of the spotlight (FIG. 2E). The lack of lateral "leakage current" in the semiconductor layer is due to its intrinsic nature, we know from impedance analysis that the resistance of the layer in the dark is in the gigaohm range.

Figure 9A:
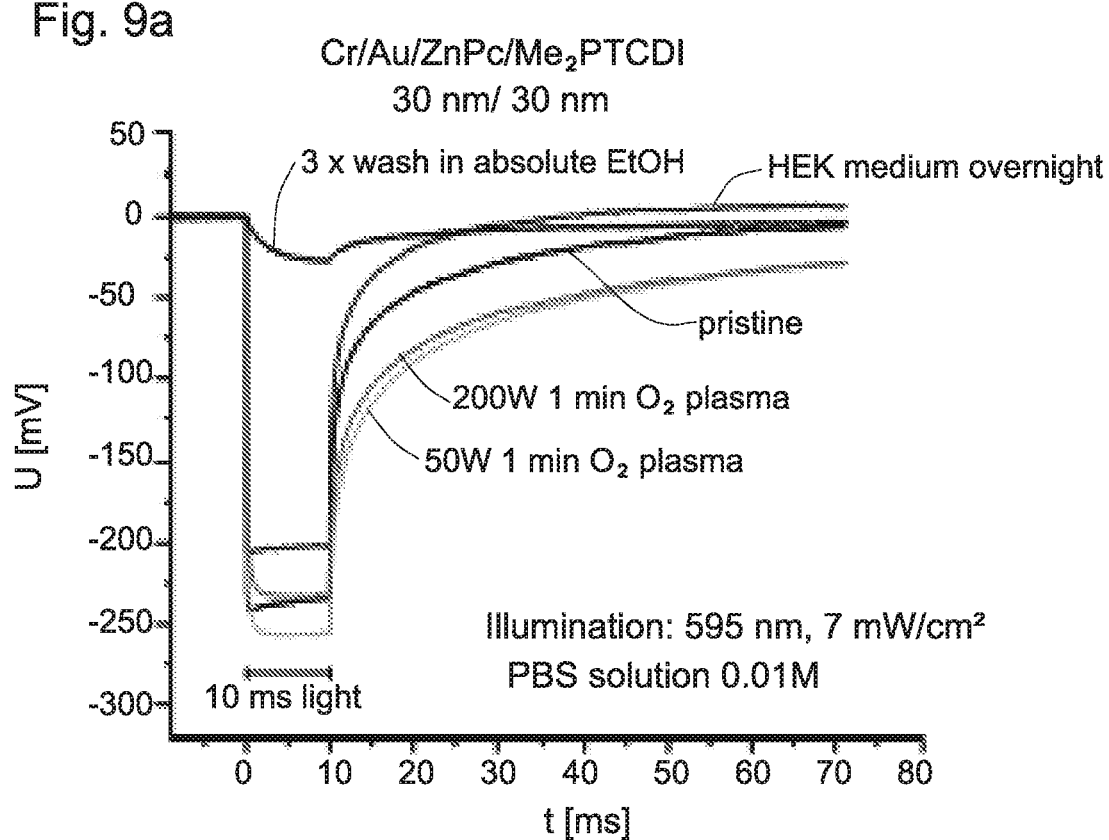
FIGS. 9A-B show that metal-containing phthalocyanines do not lead to stable operation. Measurement of photovoltages of the ZnPc/PTCDI materials pair illustrates the effects of delamination (FIG. 9A C18 free and FIG. 9B with C18).
Figure 9B:
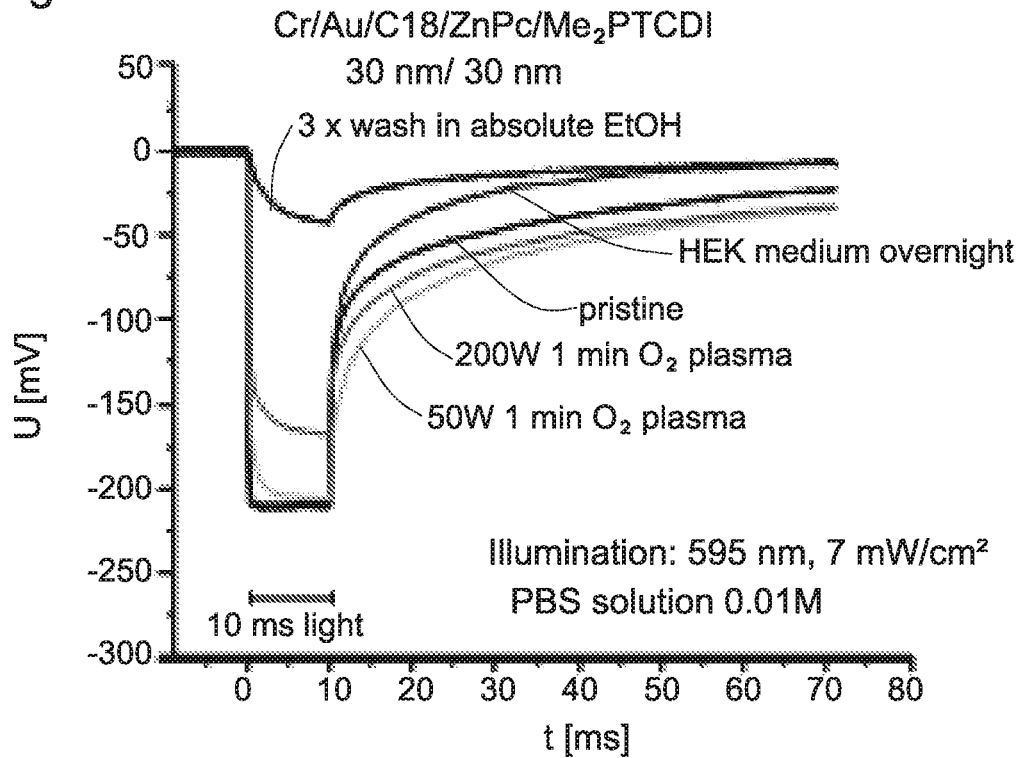

For proper operation in electrophysiological applications, devices must be stable in aqueous environments and compatible with sterilization procedures. We measured samples over several days in PBS solution without noting decrease of recorded photovoltage. Accelerated stress test involving sequential treatment with oxygen plasma, ethanol, incubation in cell culture medium, followed by UV sterilization treatment and repeated ethanol rinsing were performed to validate device stability (FIG. 2G). In this study, we fabricated also devices from the well-known metal-containing phthalocyanine derivatives with copper and zinc, CuPc and ZnPc. These performed initially at a similar level as H$_2$Pc devices, however these devices were not stable with respect to delamination and failed during these stress-test experiments (FIGS. 9A-B). The Cr/Au/H$_2$Pc/PTCDI device configuration routinely passed the entire stress test sequence without significant loss in photovoltage or visible delamination.

Photostimulation of Cultured Primary Neurons

Having established details on the relationships between device structure and photovoltage behaviour, we proceeded to demonstrate stimulation of primary neuronal cultures (FIG. 3). We compared dissociated mice cortical neurons cultured on type I sample (Cr/Au/H$_2$Pc/PTCDI, n=3) with neurons cultured on standard petri-dishes coated poly-d-lysine (PDL—a standard cell adhesion layer, n=3). After 4 days in vitro (DIV) we infected the cultures with a viral vector for expressing the calcium indicator GCaMP6 and imaged neural activity at DIV 14. All cultures on both types of substrates developed into viable neural network, exhibiting spontaneous activity as indicated by the fluorescent calcium imaging (FIGS. 3A-B). Using a pulsed light stimulation, composed of 100 pulses of 600 nm, 480 mW/cm$^2$, 5 ms pulse duration, 10 ms interpulse interval, we were able to detect a clear response only in a neuronal network that was cultured on type I device samples (FIG. 3D). It is important to note that the kinetics of the calcium indicators are relatively slow and do not show reliable single action-potential-associated calcium signals. Therefore, only a burst of activity that result from a train of pulses can accumulate into a detectable signal. In order to evidence the photocapacitive mechanism behind the observed action potential generation, we evaluated the contribution of photothermal heating (FIG. 10A-D). We utilized a calibrated pipette conductometric technique[36] to measure local heating at the p-n device surface. Using the same illumination protocol, with the pulse train of 5 ms pulses, we registered temperature increases of 0.28° C. over the timescale of 1.5 s. The magnitude of these temperature changes indicates that a photothermal effect cannot be responsible for the action potential generation observed in these neuronal cultures. These Ca imaging studies show the potential of the organic photocapacitors to stimulate action potentials and the stability of the devices in physiological environment, and furnish preliminary evidence that the materials are not detrimental to cell viability.

From Film to Pixels

Figure 4A:
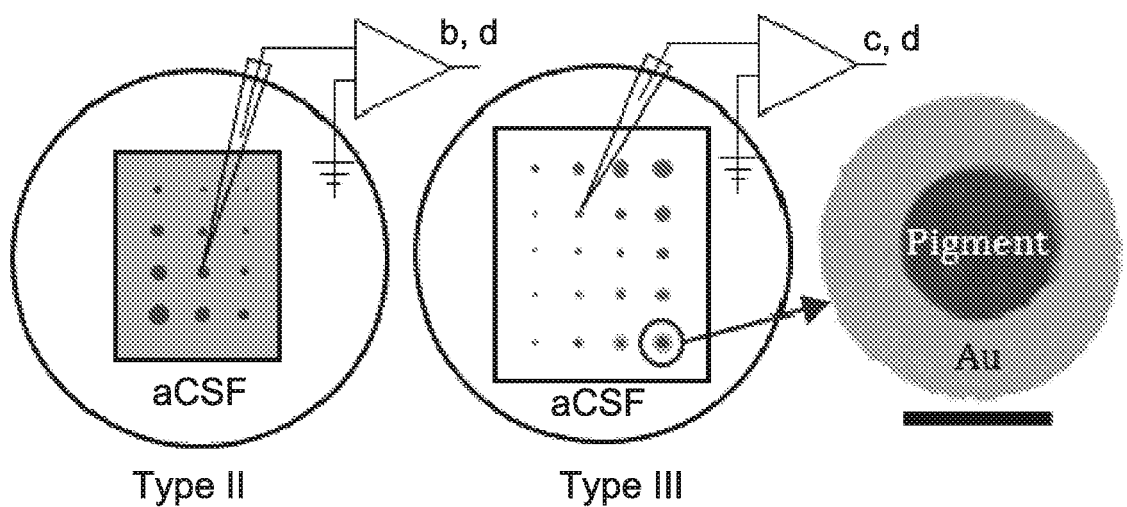
FIGS. 4A-F depicts the evolution from films to pixels.
Figure 4B:
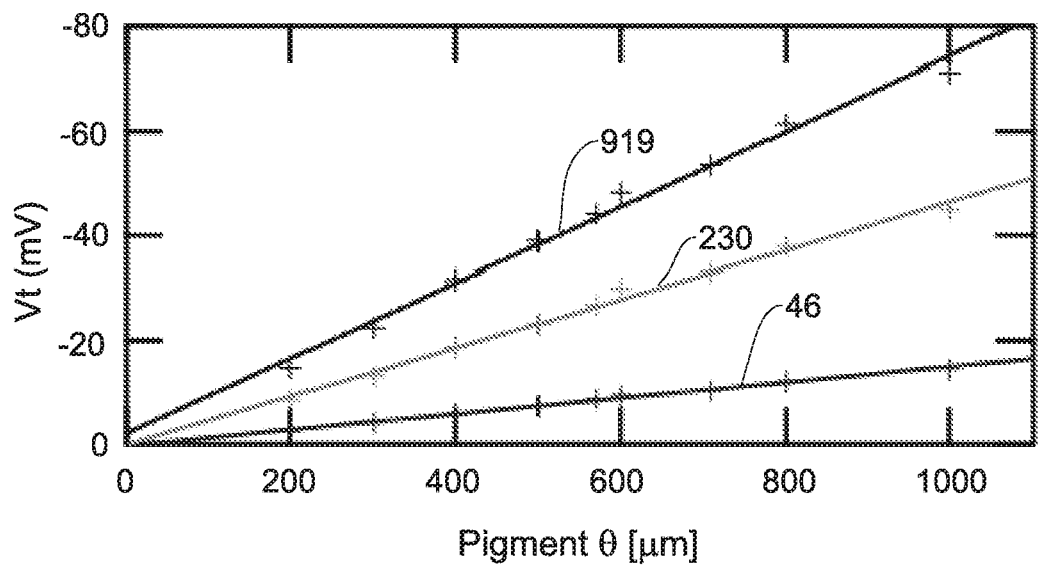
Figure 4C:
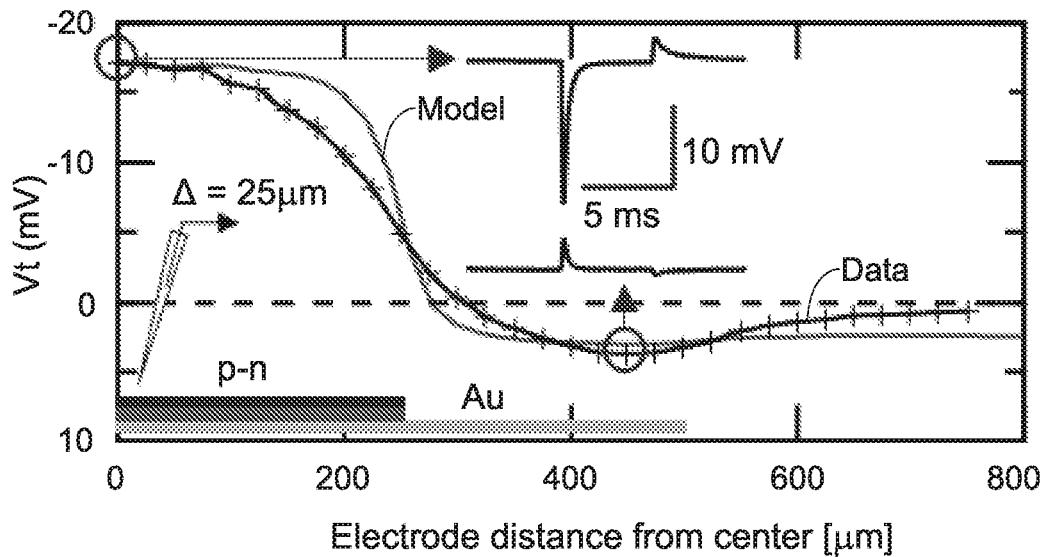
Figure 4D:
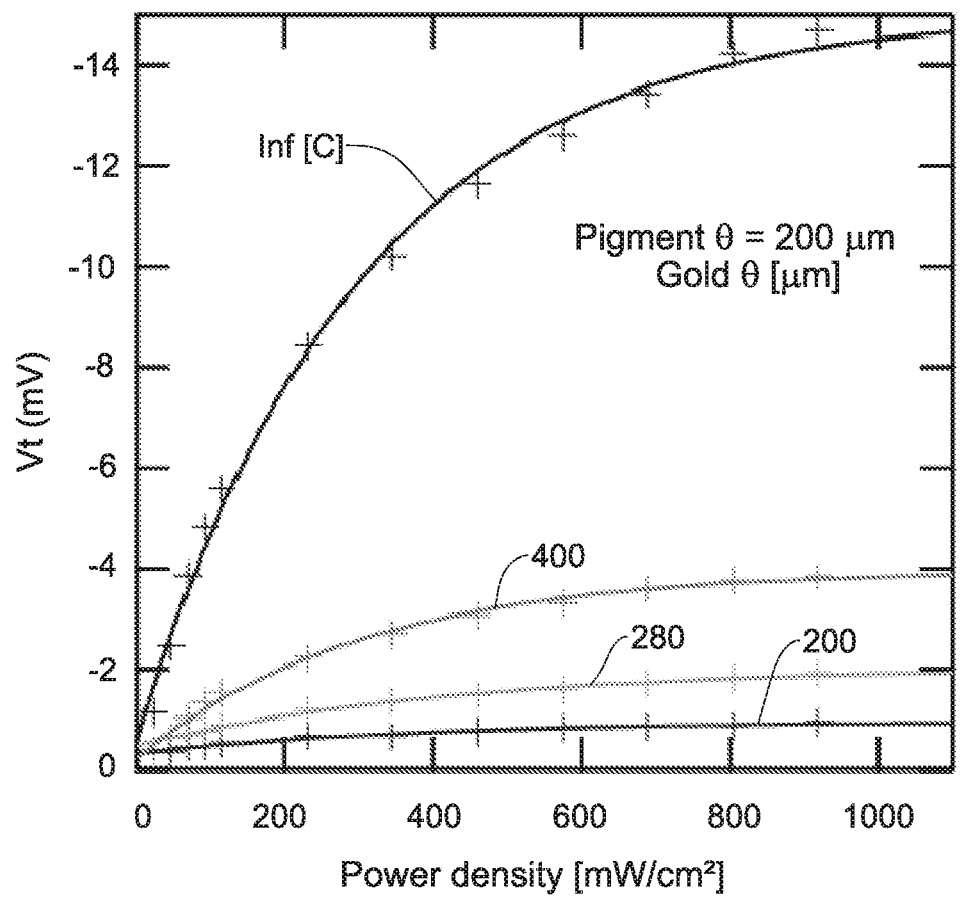
Figure 4F:
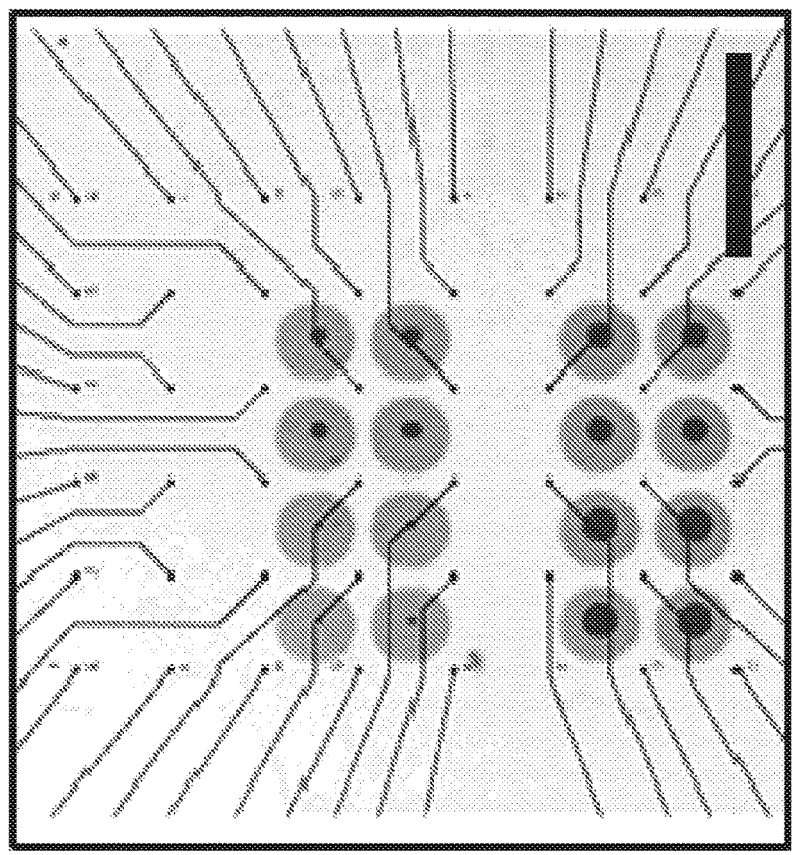
Figure 4E:
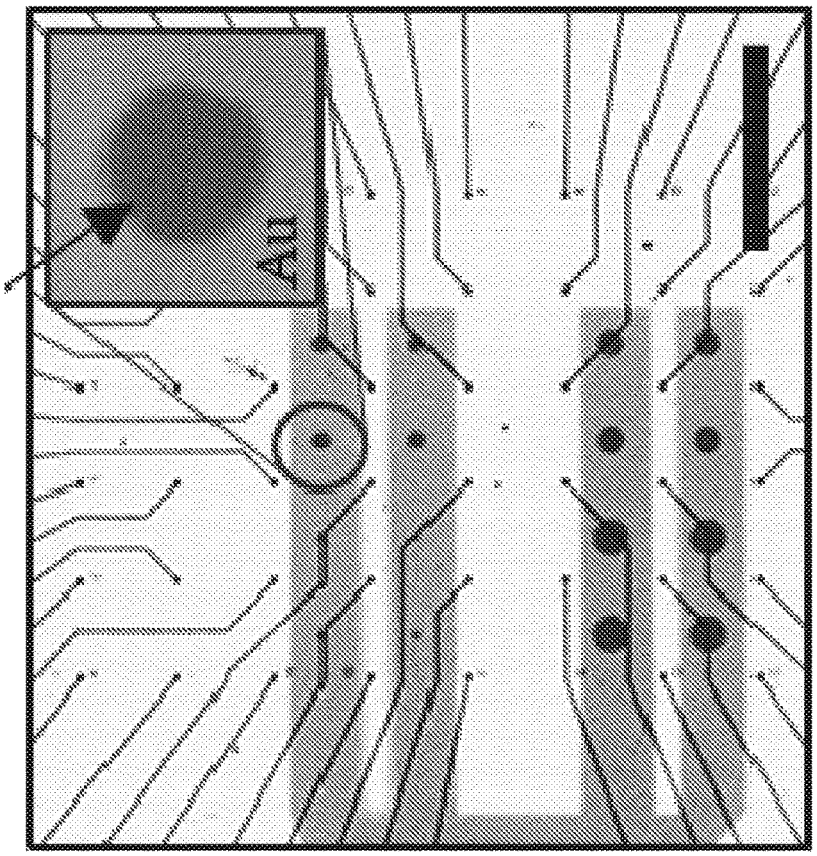

While larger uniform films are a simple platform for stimulating neurons, patterned pixels offer several possible advantages including integration with recording electrode arrays and stimulation localization. Decrease in the lateral dimensions of the device is also required for effective retinal implants or other applications requiring electrical stimulation. To design devices for effective stimulation using isolated islands, samples with p-n areas of different sizes, ranging from 200 to 1000 µm in diameter, on top of a large, (type II), or finite (type III) gold surface area were fabricated and their $V_t$ was measured as described before (FIG. 4A). We evaluated the dependence of cathodic photovoltage as a function of the sizes of both the p-n junction area and the underlying gold layer. First, we varied the size of p-n junction islands on a gold film which had hundredfold greater area than the p-n regions, which we refer to as the "infinite" gold condition (FIG. 4A, device type II). We found that photocathodic voltage scales linearly with p-n junction diameter, and that p-n junction diameter of less than 150 µm is unlikely to yield effective stimulation (FIG. 4B). It is apparent that the gold in contact with surrounding electrolyte is necessary for accommodating the positive charges photogenerated by the p-n junction. By laterally scanning the micropipette electrode from the centre of the p-n junction onto the gold layer it is clear that the sign of the recorded potential shifts from negative on top of the p-n junction to positive over the metal, and remains positive to around 250 µm away from the edge of the p-n layer (FIG. 4C). The measured potential in solution closely follows the electrostatic model, plotted together with experimental data, for potential in the vicinity of disks of charge. To quantify the effect of exposed gold on performance, the p-n junction diameter was held constant 200 µm and we varied the underlying gold size (FIG. 4A, device type III). An increased area of exposed gold is a critical parameter to obtain higher photocathodic values (FIG. 4D). Using these findings, we modified commercial MEAs with p-n pixels on large gold traces (FIG. 4E) and on 470 µm diameter gold disks (FIG. 4F), creating platforms for localized photostimulation and simultaneous neural recording.

Photostimulation of a Blind Retina Model

The embryonic chick retina is a well-established model for the development of the visual system and the retina in particular. At embryonic day 14 (E14), retinal cells are in an early maturation stage, but the retina is not yet sensitive to light. Opsins mRNA only begins to appear in a small region by then, while photoreceptor electrical activity in response to light is not detected before E17. Thus, at this stage of development, the chick retina serves as a light insensitive retinal model.

Figure 5A:
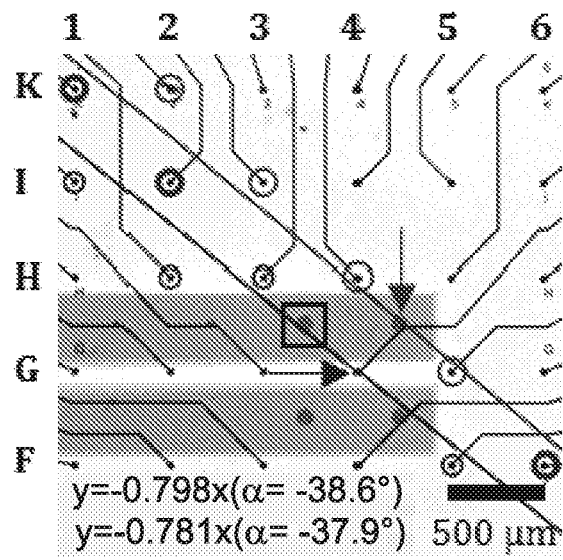
FIGS. 5A-F depicts direct responses of retinal ganglion cells (RGC) in a light-insensitive retina.
Figure 5B:
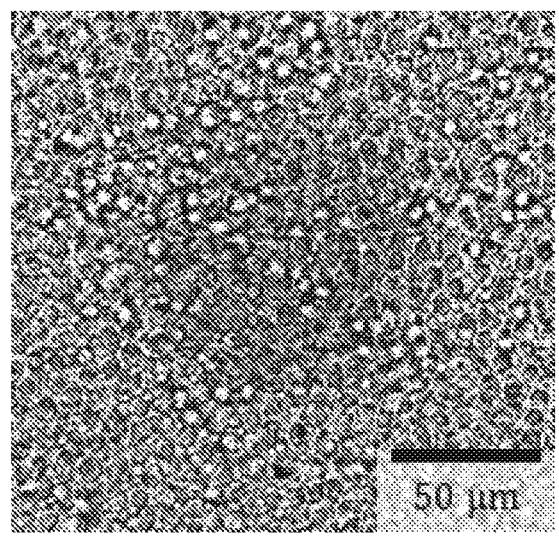
Figure 5C:
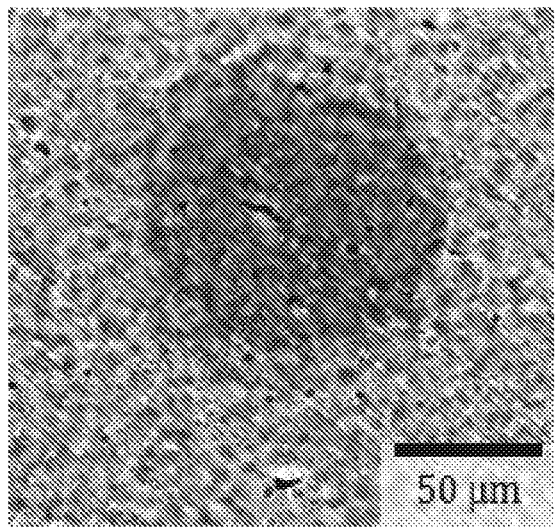
Figure 5C:
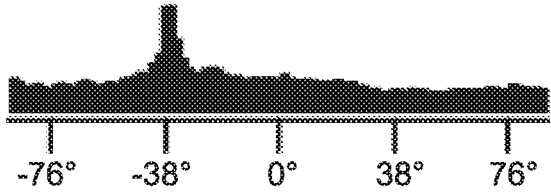
Figure 5F:
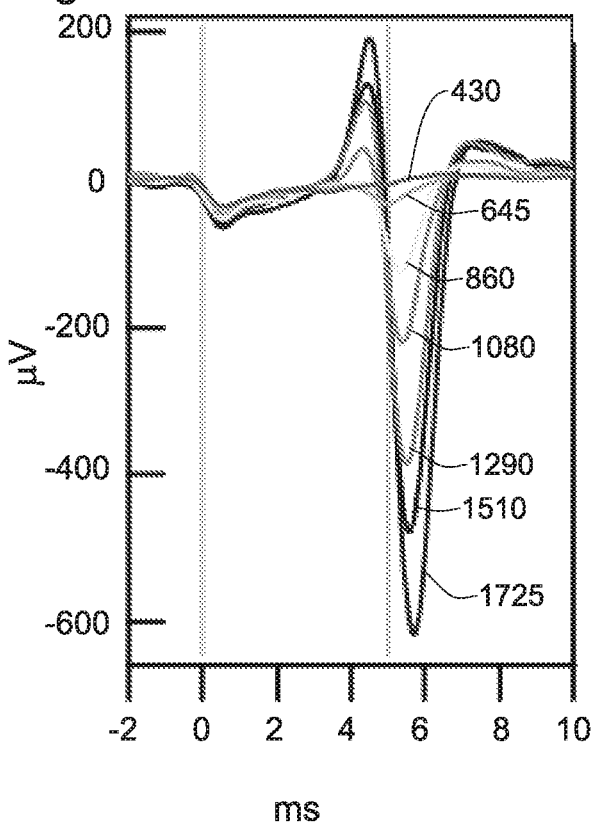
Figure 5D:
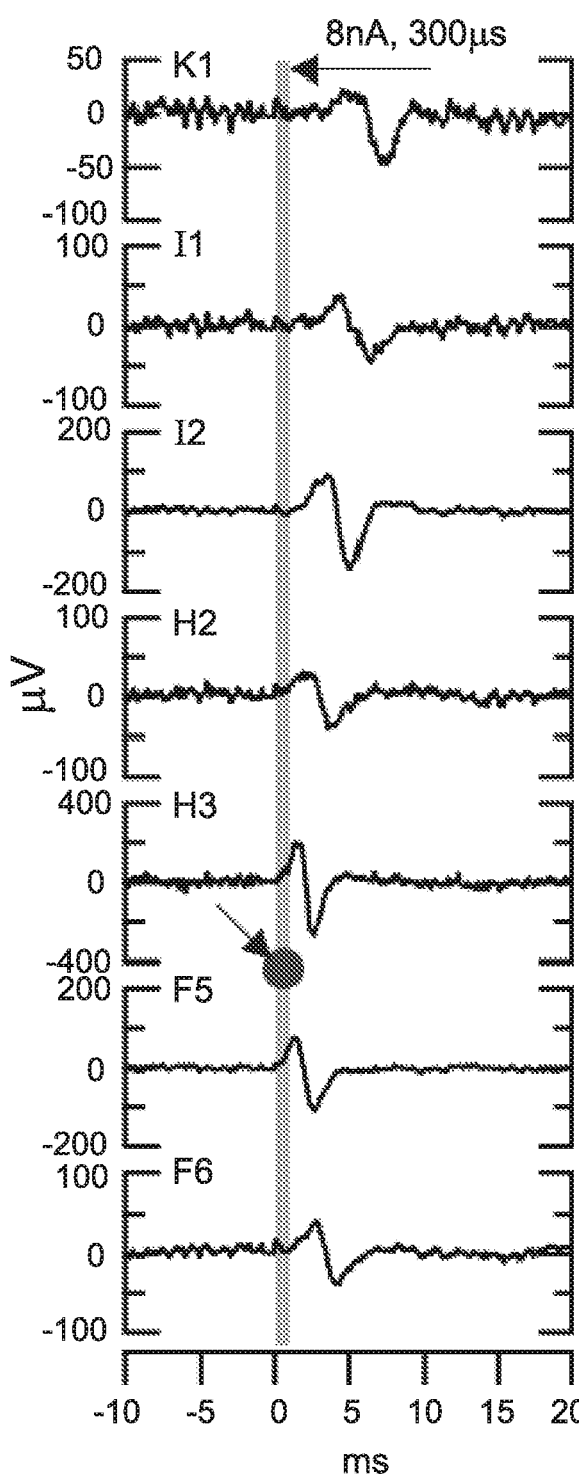
Figure 5E:
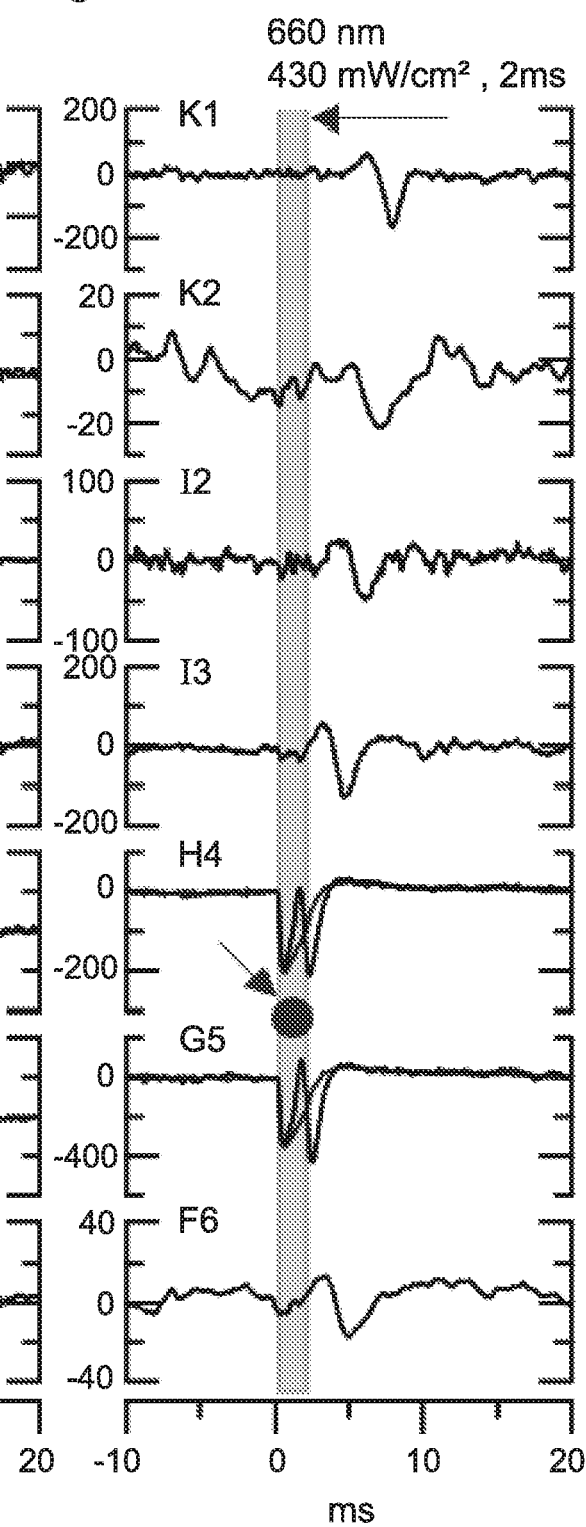

Retinas (E14) were placed on type II or type III device-modified MEAs (FIG. 5A). Outer nuclear layer (FIG. 5B) and the nerve fibre layer (FIG. 5C) are readily apparent in visual inspection with a light microscope. The intrinsic light-insensitivity is always verified prior to further experiment, though E14 seldom show any light sensitivity. To provide an internal control, we used a single MEA electrode in the mode of typical electrical stimulation, delivering 0.8 µA over 300 µs, generating a direct action-potential response in the retina (FIG. 5D). We find that the exact same direct responses are generated synchronously in ganglion cells and fibres at the vicinity of the illuminated photocapacitor device pixels by delivering a 2 ms light pulse through the objective (FIG. 5E). In the chick retina, direct responses are easily recognized as they propagate in both directions along the nerve fibres (retrograde and anterograde). The latency of a direct response becomes larger when detected on electrodes that are further away from the stimulating electrode. Indeed, measured propagation direction (red and blue regression lines in FIG. 5A) and speed of 0.33±0.045 m/s (calculated from the latency of the response between two adjacent electrodes, 500 µm apart), correspond well with fibre layer alignment (FIG. 5C) and known action potential propagation speed in the chick retina. The photocapacitive pixels elicit the same direct response as current-injected MEA electrodes (n=4 retinas), verifying that the devices are photocapacitively evoking direct retinal responses. Since these spikes are synchronized, they are summed into a large electrical signal that is superimposed on the stimulating signal. The amplitude of the recorded response is a function of the amount of recruited somas and nerve fibres that is directly correlated with the stimulus light intensity (FIG. 5F). Both type II and type III samples were found to evoke direct responses in retinas. Successful stimulations were made with all pixels of 100 µm diameter and above for pulse duration as short as 1 ms. The minimal intensities for detecting a response were 430 mW/cm$^2$ and 130 mW/cm$^2$ for 100 and 200 µm diameter pixels, respectively. These results unambiguously show deterministic and rapid action potential generation in light-insensitive retinas.

Discussion

The devices studied are free-standing (electrically-floating structures) and are fabricated via scalable fabrication steps where the substrate remains at room temperature, which allows integration with arbitrary substrate materials. While silicon based photodiodes have so far played a dominant role in the realm of artificial photoelectrical stimulation of neurons, silicon devices have several shortcomings compared with organic pigment layers. First, pigment films have a higher absorbance coefficient, allowing them to efficiently absorb light. At 660 nm, used in this work, the absorbance coefficient of vacuum-evaporated $H_2Pc$ is $3\times10^5$ cm$^{-1}$, while silicon is $2.58\times10^3$ cm$^{-1}$. This difference allows making thinner photoactive films much less invasive, as the devices can have thicknesses that are much smaller than single cells. Our devices are 500 times thinner than the thinnest state-of-the-art silicon diodes for retinal implants. Moreover, in our design, one has a nanostructured semiconductor surface in direct contact with the electrolytic medium/biological sample, there is no voltage drop on a passivation layer or on conducting interconnects in between. Silicon photocapacitive devices charge metal electrodes—here we have the semiconductor surface itself serving as the primary charge-carrying electrode. Secondary metal electrodes must be employed in the case of silicon since it is not stable in physiological aqueous media. It must be carefully encapsulated, and interconnects passivated using $SiO_2$/$Si_3N_4$ layers, for example. The organic p-n layers can make direct contact with the physiological environment due to their durability. Organic crystalline pigments like phthalocyanine and perylene bisimides are famously indestructible in terms of chemical and photochemical stability. Further, the nontoxicity of both phthalocyanines and perylene pigments is well-documented. These materials are used in cosmetics, medical products, and tattoos. They are commercial colorants which belong to the lowest category of hazard and toxicity for consumer approved materials in the EU.

Achieving temporal control over neural stimulation requires activation with short latency of the response. In the case of retinal stimulation, such short latency responses are attributed to directly activating the retinal ganglion cells (RGCs), when the electrodes are placed on top of the inner limiting membrane (ILM) at the epiretinal side, or to the inner nuclear layer (INL), when the electrodes are positioned subretinally, next to the degenerated photoreceptors. Direct activation of RGCs means that each stimulation pulse produces short latency synchronized action potentials (AP) in several somas and axons of RGCs that are located at the vicinity of stimulating electrode. On the contrary, stimulation of inner retinal neurons results in the generation of bursts of unsynchronized spikes in the RGCs with much longer latency, due to synapse transmission. Therefore, a major challenge in neuronal activation, in particular with photosensitive nanostructures, is to understand and to control the mechanism by which the activation is achieved, aiming for a sufficient charge injection for obtaining direct electrical activation similar to that of the best-optimized silicon-based electronics. Moreover, such electrical stimulation should be capacitive, which is considered safe and can be used for extended duration, unlike faradaic stimulation and thermal activation that are not considered optimal and should be avoided.

The retinal setup involves laying the RGC on top of the organic pigment, as in the case of epiretinal stimulation, while illuminating from the direction of the photoreceptors. This light trajectory is opposite to what is normal physiologically, but it does not contradict with the focus of this work, showing that the photoelectric transduction of our device is sufficient to stimulate neural tissue in a direct electrical manner at safe light intensities. In terms of neuronal stimulation benchmark parameters, our ultrathin organic device reaches parity with the state-of-the-art silicon diode-based technologies. This presents the ability to evoke action potentials in retinas using the same light intensity range as triple-tandem silicon retinal stimulation diodes. The range of pulsed light intensities and durations we have used has been deemed two orders of magnitude below the safe limit for ocular stimulation. Moreover, 660 nm is within the biological tissue transparency window, which can enable a host of other applications in peripheral nerve stimulation.

To conclude, we demonstrated a new and advantageous concept to photostimulate neurons. Primary neurons were cultured on our photocapacitor devices for three weeks, demonstrating viability of both the devices and the cells. The latter could readily be photostimulated using short impulses of light. We next integrated photocapacitors onto commercial MEAs, enabling simultaneous photoexcitation and recording. Using this platform, we demonstrated effective direct photostimulation of light-insensitive embryonic chicken retinas. The MEA allows us to make an in situ control of conventional electrical stimulation, thereby we verify that the photocapacitor arrays and the electrical stimulation have the exact same retinal response. We experimentally discount the presence of photothermal heating effects. The culmination of this work are stand-alone photocapacitors with organic pixels of 100 µm in diameter to locally and reproducibly evoke action potentials. Future research of this device concept should involve optimizing materials to afford higher responsivity and photovoltage, allowing smaller pixels and lower light intensities. Different nano- and microstructuring of the organic material must be explored to yield optimal coupling with cells. The technology is a new platform that can interact with living cells via a true capacitive coupling mechanism, thus enabling safe and versatile next-generation implant technologies, and already at the level demonstrated here is suitable for various in vivo applications in peripheral or central nervous system stimulation, for example in the context of traumatic injury. Success in these efforts requires deployment of the devices on implantable and/or bioresorbable substrates, and evaluation of their stability and performance in vivo.

The invention claimed is:

1. A method for stimulating an excitable tissue or cell, the method comprising:
    placing or positioning into, onto or in the contact with a target excitable tissue or cell at least one photoresponse device comprising a multilayer comprising at least one metal or a conductive material layer and p-n/n-p structure layered thereon, the p-n/n-p structure comprising semiconducting organic nanocrystals, and focusing light with a wavelength between 400-2,000 nanometers onto the device, to thereby cause a photoresponse effect comprising an electrical pulse, and stimulation of the excitable tissue or cells, when said device and said tissue or cells are in a physiological medium;
    wherein the p-n/n-p structure in said device is in continuous contact with the at least one metal or the conductive material layer,
    wherein the at least one metal or the conductive material layer is configured to be in electrical contact with the physiological medium in which the device operates, the p-n/n-p structure comprising a combination of two or more organic semiconductor pigments, at least one being selected amongst electron donor materials comprising a p-type material, and at least one other selected amongst electron accepting materials comprising an n-type material; and
    wherein the device is a photocapacitor.

2. The method according to claim 1, wherein the device comprises a metal layer or a conductive material layer, a layer of at least one light-absorbing, electron donor material that is in continuous contact with the metal or the conductive material layer and a layer of at least one electron acceptor material that is in continuous contact with the layer of the at least one light-absorbing material.

3. The method according to claim 1, wherein the device comprises a metal layer or a conductive material layer, a layer of at least one electron acceptor material that is in continuous contact with the metal or the conductive material layer and a layer of at least one light-absorbing, material that is in continuous contact with the layer of the at least one electron acceptor material.

4. The method according to claim 1, wherein said device comprises a substrate, at least one metal layer or a conductive material layer formed onto one or more regions of the substrate, and a p-n/n-p structure formed on at least one of the metal layer or metal regions.

5. The method according to claim 1, wherein the device comprises a metal layer or a conductive material layer, a layer consisting of at least one p-type organic pigment material or a layer consisting of at least one n-type organic pigment material that is stacked onto at least a region of said metal layer.

6. The method of claim 1, wherein said p-n/n-p structure in said device is a p-n structure or an n-p structure.

7. The method of claim 6, wherein said p-type material is a metal containing or metal free phthalocyanine.

8. The method of claim 1, wherein said n-type material is N,N'-dimethyl perylenetetracarboxylic diimide.

9. The method of claim 1, wherein said target excitable tissue is the retina.

10. A method of generating an electrical pulse on a biological tissue or cell, the method comprising positioning into, onto or in contact with a target excitable tissue or cell at least one photoresponse device comprising including a multilayer comprising at least one metal or a conductive material and p-n/n-p structure layered thereon, the p-n/n-p structure comprising semiconducting organic nanocrystals; and focusing light with a wavelength between 400-2,000 nanometers onto the device, to thereby generate an electrical pulse, when said device and said biological tissue or cells are in a physiological medium;

wherein the p-n/n-p structure in said device is in continuous contact with the at least one metal or the conductive material layer,
   wherein the at least one metal or the conductive material layer is configured to be in electrical contact with the physiological medium in which the device operates, the p-n/n-p structure comprising a combination of two or more organic semiconductor pigments, at least one being selected amongst electron donor materials comprising a p-type material, and at least one other selected amongst electron accepting materials comprising an n-type material; and
   wherein the device is a photocapacitor.

11. The method according to claim 10, wherein the device comprises a metal layer or a conductive material layer, a layer of at least one light-absorbing, electron donor material that is in continuous contact with the metal or the conductive material layer and a layer of at least one electron acceptor material that is in continuous contact with the layer of the at least one light-absorbing material.

12. The method according to claim 10, wherein the device comprises a metal layer or a conductive material layer, a layer of at least one electron acceptor material that is in continuous contact with the metal or the conductive material layer and a layer of at least one light-absorbing, electron donor material that is in continuous contact with the layer of the at least one electron acceptor material.

13. The method according to claim 10, wherein said device comprises a substrate, at least one metal layer or a conductive material layer formed onto one or more regions of the substrate, and a p-n/n-p structure formed on at least one of the metal layer or metal regions.

14. The method according to claim 10, wherein the device comprises a metal layer or a conductive material layer, a layer consisting of at least one p-type organic pigment material or a layer consisting of at least one n-type organic pigment material that is stacked onto at least a region of said metal layer.

15. The method of claim 10, wherein said p-n/n-p structure in said device is a p-n structure or an n-p structure.

16. The method of claim 15, wherein said p-type material is a metal containing or metal free phthalocyanine.

17. The method of claim 10, wherein said n-type material is N,N'-dimethyl perylenetetracarboxylic diimide.

18. The method of claim 10, wherein said target excitable tissue is the retina.

* * * * *

UNITED STATES PATENT AND TRADEMARK OFFICE
CERTIFICATE OF CORRECTION

PATENT NO. : 12,070,597 B2  
APPLICATION NO. : 16/766978  
DATED : August 27, 2024  
INVENTOR(S) : Yael Hanein et al.

Page 1 of 1

It is certified that error appears in the above-identified patent and that said Letters Patent is hereby corrected as shown below:

In the Claims

Claim 3, Column 20, Line 43:  
Delete: "light-absorbing, material"  
Replace with: light-absorbing, electron donor material Signed and Sealed this  
Twenty-first Day of October, 2025

John A. Squires  
*Director of the United States Patent and Trademark Office*